United States Patent [19]
Ehrlich et al.

[11] Patent Number: 6,133,275
[45] Date of Patent: Oct. 17, 2000

[54] 3-PHENYLPYRROLIDINE ALPHA-1 ADRENERGIC COMPOUNDS

[75] Inventors: Paul P. Ehrlich, Guliford, Conn.;
Jeffrey W. Ralston, Chicago, Ill.;
Jerome F. Daanen, Racine, Wis.;
Michael D. Meyer, Lake Villa, Ill.

[73] Assignee: Abbott Laboratories, Abbott Park, Ill.

[21] Appl. No.: 09/073,555

[22] Filed: May 6, 1998

[51] Int. Cl.[7] .................. C07D 495/14; C07D 493/14; A61K 31/4985
[52] U.S. Cl. .................. 514/267; 544/250; 544/251
[58] Field of Search ................ 514/267; 544/250, 544/251

[56] References Cited

U.S. PATENT DOCUMENTS

| | | | |
|---|---|---|---|
| 3,719,667 | 3/1973 | Gutowski | 260/239.1 |
| 3,840,556 | 10/1974 | Kukolja | 260/326.5 |
| 4,670,560 | 6/1987 | Press et al. | 544/278 |
| 4,835,157 | 5/1989 | Press et al. | 514/183 |
| 4,939,137 | 7/1990 | Russell et al. | 514/183 |
| 5,304,560 | 4/1994 | Shimazaki et al. | 514/259 |
| 5,521,181 | 5/1996 | Meyer et al. | 514/249 |
| 5,597,823 | 1/1997 | Meyer et al. | 514/250 |
| 5,891,882 | 4/1999 | Meyer et al. | 514/267 |

OTHER PUBLICATIONS

Chapple, et al., British Journal Urology, vol., 63, pp. 487–496, 1989.
Janknegt, et al., European Urology, vol. 24, pp. 319–326, 1993.
Lepor, et al., Journal Urology, vol. 145, p. 263A, 1991.
Chow, et al., British Journal Urology, vol. 65, pp. 36–38, 1990.
Chapple, et al., Urology Int. vol. 45, pp. 47–55, 1990.
Andersson, Scandinavian Journal Urology and Nephrol., vol. 30, pp. 105–111, 1996.
Greengrass, et al., European Journal Pharmacology, vol. 55, pp. 323–326, 1979.
Hancock, et al., Journal Receptor Res., vol. 8, pp. 23–46, 1988.
Lee, C., et al., "Pharmacological characterization of LB50016, N–(4–amino)butyl 3–phenylpyrrolidine derivative, as a new 5–HT1A receptor agonist", *Chemical Abstracts*, Accession No. 131:74969 (1999).

*Primary Examiner*—Mukund J. Shah
*Assistant Examiner*—Deepak R. Rao
*Attorney, Agent, or Firm*—Frank Z. Yang; Lawrence S. Pope; Michael J. Ward

[57] ABSTRACT

Compounds having the formula

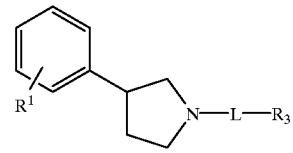

are $\alpha_1$ adrenoreceptor antagonists. Processes for making these compounds, synthetic intermediates employed in these processes and a method for inhibiting $\alpha_1$ adrenoreceptors and treating benign prostatic hyperplasia (also called benign prostatic hypertrophy or BPH) and other urological diseases such as BOO (bladder outlet obstruction), neurogenic bladder and gynecological syndromes such as dysmenorrhea are disclosed.

15 Claims, No Drawings

3-PHENYLPYRROLIDINE ALPHA-1 ADRENERGIC COMPOUNDS

TECHNICAL FIELD

The present invention relates to novel alpha-1 adrenoreceptor antagonists ($\alpha_1$ antagonists), processes for making such compounds, synthetic intermediates employed in these processes and methods of inhibiting $\alpha_1$ adrenoreceptors for treating urological diseases such as BPH (benign prostatic hyperplasia), BOO (bladder outlet obstruction) and neurogenic bladder and gynecological syndromes such as dysmenorrhea.

BACKGROUND OF THE INVENTION

Adrenergic neurons play a major role in innervating heart, blood vessel and smooth muscle tissue. Compounds capable of interacting with adrenoreceptor sites within adrenergic nerves can initiate a variety of physiological responses including vasodilation, vasoconstriction and increased or decreased heart rate (chronotropic), contractility (inotropic) and metabolic activity. Various adrenergic compounds have been previously employed to affect these and other physiological responses. However, many adrenergic compounds do not possess significant selectivity to enable desirable interactions with adrenergic adrenoreceptor sites. That is, these adrenergic compounds do not demonstrate a high degree of specificity for differing adrenoreceptor types within adrenergic neurons. Accordingly, they cannot selectively induce a desired physiological response apart from other possible, perhaps less desirable, responses.

Benign prostatic hyperplasia (also known as benign prostatic hypertrophy or BPH) is a condition which develops in middle-aged and elderly males and refers to the benign overgrowth of the stromal and epithelial elements of the prostate. Symptoms of BPH include increased frequency of urination, nocturia, a weak urine stream and hesitancy or delay in starting the urine flow. Chronic consequences of BPH can include hypertrophy of bladder smooth muscle, a decompensated bladder and an increased incidence of urinary tract infection.

The large numbers of α-adrenergic adrenoreceptors in the smooth muscle of the prostatic capsule and bladder neck indicate both a static and a dynamic component to bladder outlet obstruction associated with BPH. The static component derives from the progressive hyperplasia of the prostate with aging and leads to urethral narrowing which causes symptoms of urinary obstruction. In addition to this essentially mechanical problem, the amount of smooth muscle contraction controlled by the sympatheic nervous system varies with stress, cold and sympathomimetic drugs. This dynamic component explains the often rapid fluctuations in symptoms observed in patients with prostatism.

Currently, The most effective treatment for BPH is the surgical removal of the obstructing tissue, a treatment directed to both the static and dynamic components of BPH. However, this surgery has a 1% mortality rate in addition to significant risks of other adverse events (2–4% incontinence, 5–10% infection and 5–10% impotence).

Researchers have come to recognize the potential role of selective $\alpha_1$ adrenoreceptor blockade in diseases of the lower urinary tract. Studies by several groups have documented the relative roles of $\alpha_1$ adrenoreceptors and $\alpha_2$ adrenoreceptors in the stromal compartment of the prostate, thereby providing a putative molecular basis for using $\alpha_1$ adrenoreceptor specific blockers ($\alpha_1$ antagonists) in the non-surgical management of BPH. Chapple et al., *Br. J. Urol.*, v. 63, pp. 487–496 (1989). Clinical efficacy of $\alpha_1$ antagonists in BPH has been demonstrated with several non-selective $\alpha_1$ blockers including terazosin (Hytrin®), prazosin and doxazosin. Treatment periods as short as two to four weeks with $\alpha_1$ adrenoreceptor blockers have shown objective improvements in the mean and maximum urinary flow rates (14–96%) with subjective improvements in patients' symptom scores. Janknegt et al., *Eur. Urol.*, v. 24, pp. 319–326 (1993). Longer term studies with terazosin, indoramin, prazosin and doxazosin have similarly demonstrated significant improvements in urinary flow rates and subjective symptom scores. Lepor et al., *J. Urol.*, v. 145, p. 263A (1991); Chow et al., *Br. J. Urol.*, v. 65, pp. 36–38 (1990); Chapple et al., *Urol. Int.*, v. 45, pp. 47–55 (1990). However, these agents possess similar dose-limiting side-effects such as hypotension, dizziness and muscle fatigue.

In recent years, it has become clear that BPH and bladder outlet obstruction (BOO) are clinically differentiable and that the severity of clinical BPH is related to many factors in addition to BOO. For example, BOO may be related to other urological symptoms such as detrusor instability. In addition, researchers postulate that $\alpha_1$ adrenoreceptors outside of the prostate are also important in the etiology of lower urinary tract symptoms. They conclude that antagonizing these receptors in spinal cord, ganglia, nerve terminals, bladder and bladder neck or the external urethral sphincter can be important in the pharmacotherapy of urological conditions such as BOO and neurogenic bladder. Andersson, *Scand. J. Urol. and Nephrol.*, v. 30, pp. 105–11 (1996).

Scientists have recognized that women possess paraurethral glands are anatomically, histologically and biochemically similar to the male prostate. This suggests a potential role for $\alpha_1$ antagonist pharmacotherapy for ameliorating some symptoms of female urethral syndromes. In addition, researchers have also observed that α-adrenoreceptors are functionally important to smooth muscle contraction in the uterus and that the modulation of sympathetic responses to catecholamines is enhanced by elevated levels of estrogens. This is consistent with the increased α-adrenoreceptor response and receptor density following estrogen administration to animals. Thus hormonal regulation of $\alpha_1$ adrenoreceptor sensitivity could play a role in enhanced uterine contractions in dysmenorrhea, a condition for which selective $\alpha_1$ antagonists could have therapeutic potential.

It is apparent that a need exists for a "uroselective" $\alpha_1$ antagonist with reduced side effects.

SUMMARY OF THE INVENTION

The present invention provides a compound of formula (I)

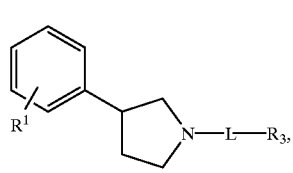

(I)

or a pharmaceutically acceptable salt, ester or prodrug thereof, wherein $R_1$ represents 1 or more optional substituents independently selected from the group consisting of $C_{1-8}$ alkyl;

$C_{2-8}$ alkenyl;

$C_{2-8}$ alkynyl;

alkoxyalkyl, wherein the alkyl and alkylene groups are independently $C_{1-8}$;

$C_{1-8}$ alkoxy;

$C_{1-8}$ alkoxycarbonyl;

hydroxy;

$C_{1-8}$ hydroxyalkyl;

carboxy;

O-protected carboxy;

$C_{1-8}$ carboxyalkyl;

O-protected $C_{1-8}$ carboxyalkyl;

halo;

amino;

N-protected amino;

$C_{1-8}$ aminoalkyl; and $C_{1-8}$ N-protected aminoalkyl;

L is $C_{2-8}$ alkylene; and $R_3$ is selected from the group consisting of (1)
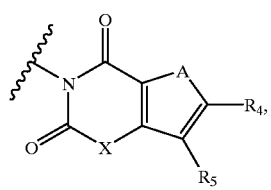

(2)
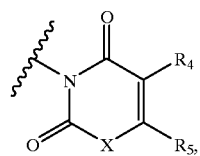

(3)
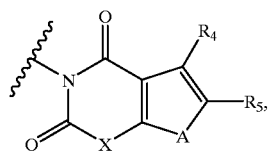

(4)
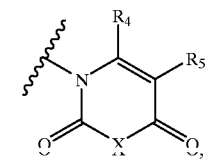

(5)
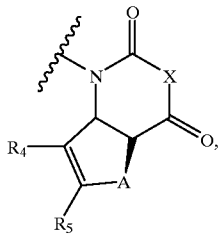

-continued (6)
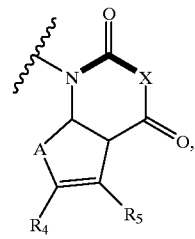

(7)
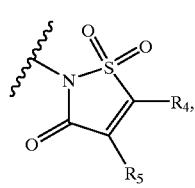

(8)
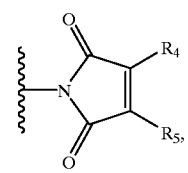

(9)
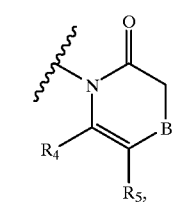

(10)
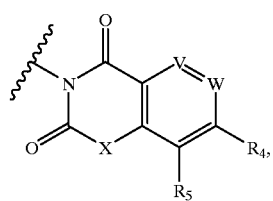

(11)
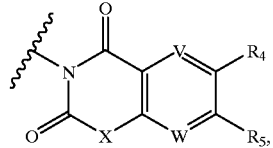

(12)
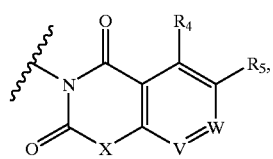

-continued

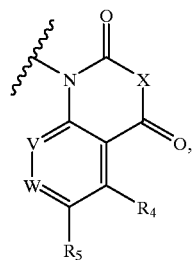

(13)

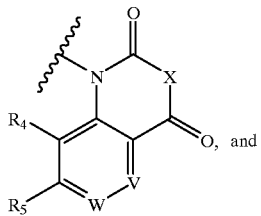

(14)

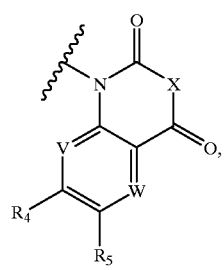

(15)

wherein, for (1) through (15), $R_4$ and $R_5$ together form a ring which is fused to its adjacent ring and is selected from the group consisting of
- (a) a five-membered carbocyclic ring and
- (b) a five-membered ring having four carbon atoms and one heteroatom selected from the group consisting of
  nitrogen,
  oxygen, and
  sulfur;
- (c) a five-membered ring having three carbon atoms and two heteroatoms independently selected from the group consisting of
  nitrogen,
  oxygen, and
  sulfur;
- (d) a six-membered carbocyclic ring;
- (e) a six-membered ring having five carbon atoms and one heteroatom selected from the group consisting of
  nitrogen,
  oxygen, and
  sulfur;
- (f) a six-membered ring having four carbon atoms and two heteroatoms selected from the group consisting of
  nitrogen,
  oxygen, and
  sulfur;
  - (g) a six-membered ring having three carbon atoms and three heteroatoms selected from the group consisting of
    nitrogen,
    oxygen, and
    sulfur;

wherein the five-membered rings formed by $R_4$ and $R_5$ together with the ring to which they are fused have 1 or 2 double bonds, and wherein the six-membered rings formed by $R_4$ and $R_5$ together with the ring to which they are fused have 1, 2 or 3 double bonds, and wherein the rings formed by $R_4$ and $R_5$ together are optionally substituted with one or two substituents independently selected from the group consisting of
  $C_{1-8}$ alkyl;
  $C_{1-8}$ alkoxy;
  cyano;
  nitro;
  carboxy;
  $C_{1-8}$ alkoxycarbonyl;
  halo;
  $C_{3-8}$ cycloalkyl;
  aryl; and
  heterocycle,
V and W are independently selected from the group consisting of
  nitrogen and
  methine;
B is selected from the group consisting of
  —O—;
  —S(O)$_t$—, wherein t is zero to two;
  —(CH$_2$)$_n$—, wherein n is one or two; and
  —NR$_6$—, wherein wherein $R_6$ is selected from the group consisting of hydrogen,
  $C_{1-8}$ alkyl;
  $C_{2-8}$ alkenyl;
  $C_{2-8}$ alkynyl;
  $C_{1-8}$ alkoxy;
  alkoxyalkyl, wherein the alkyl is $C_{1-8}$, and the alkylene is $C_{2-8}$;
  $C_{1-8}$ alkoxycarbonyl;
  hydroxy;
  $C_{1-8}$ hydroxyalkyl;
  $C_{1-8}$ carboxyalkyl;
  $C_{1-8}$ alkylsulfonyl; and
  $C_{2-8}$ aminoalkyl; and
A and X are independently selected from the group consisting of
  —O—;
  —S(O)$_t$—, wherein t is zero to two, and
  —NR$_6$—.

The present invention also relates to pharmaceutical compositions which comprise a therapeutically effective amount of a compound of formula (I) in combination with a pharmaceutically effective carrier.

The present invention also relates to a method of antagonizing $\alpha_1$ adrenoreceptor binding in a host mammal, particularly humans, by administering a therapeutically effective amount of a composition comprising a compound of formula (I). In particular, the present invention relates to a method of treating BPH, BOO or neurogenic bladder in a mammal, particularly humans, by administering to a mammal an effective amount of a compound of formula (I).

The invention further relates to a method of treating uterine smooth muscle contraction in a female host mammal, in particular humans, in need of such treatment by administering a therapeutically effective amount of a compound of formula (I).

DETAILED DESCRIPTION OF THE INVENTION

The term "alkoxy," as used herein, represents an alkyl group attached to the parent molecular group through an oxygen atom. Alkoxy groups are exemplified by methoxy, ethoxy, isopropoxy and the like.

The term "alkoxyalkyl," as used herein, represents an alkyl group to which is attached an alkoxy group. Alkoxyalkyl groups are exemplified by methoxymethyl, isopropoxyethyl and the like.

The term "alkoxycarbonyl," as used herein, represents an ester group, i.e. an alkoxy group attached to the parent molecular group through a carbonyl group. Alkoxycarbonyl groups are exemplified by methoxycarbonyl, ethoxycarbonyl and the like.

The term "alkyl," as used herein, represents a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, neopentyl and the like.

The term "alkenyl," as used herein, represents a monovalent straight or branched chain of carbon atoms containing at least one carbon-carbon double bond derived from an alkene by the removal of one hydrogen atom. Alkenyl groups are exemplified by ethenyl, 1-propenyl, 2-propenyl, 2-methyl-1-propenyl, 1-butenyl, 2-butenyl and the like.

The term "alkynyl," as used herein, represents a monovalent straight or branched chain of carbon atoms containing at least one carbon-carbon triple bond derived from an alkyne by the removal of one hydrogen atom. Alkynyl groups are exemplified by ethynyl, 1-propynyl, 2-pentynyl and the like.

The term "amino," as used herein, represents an —$NH_2$ group.

The term "aminoalkyl," as used herein, represents an alkyl group substituted by an amino group. Aminoalkyl groups are exemplified by aminomethyl, 2-aminopropyl, 3-aminopentyl and the like.

The term "aryl," as used herein, represents a mono- or bicyclic carbocyclic group having one or two aromatic rings. Aryl groups are exemplified by phenyl, naphthyl, 1,2-dihydronaphthyl, 1,2,3,4-tetrahydronaphthyl, fluorenyl, indanyl, indenyl and the like.

The term "carboxy," as used herein, represents a —$CO_2H$ group.

The term "carboxyalkyl," as used herein, represents an alkyl group substituted by a carboxy group.

The term "cyano," as used herein, represents a —C≡N group.

The term "cycloalkyl," as used herein, represents a monovalent saturated cyclic hydrocarbon group. Cycloalkyl groups are exemplified by cyclopropyl, cyclobutyl, cyclopentyl, cyclohexyl, cycloheptyl, bicyclo[2.2.1]heptyl and the like.

The term "halo," as used herein, represents F, Cl, Br and I.

The term "heterocycle," as used herein, represents represents a 6-membered ring containing one or two nitrogen atoms and three double bonds. Heterocycles are exemplified by pyridine and pyrazine and may be optionally substituted with halo, alkoxy, phenyl or substituted phenyl.

The term "hydroxy," as used herein, represents an —OH group.

The term "hydroxyalkyl," as used herein, represents an alkyl group substituted by one, two or three hydroxy groups, with the proviso that no more than one hydroxy group may be attached to a single carbon atom of the alkyl group. Hydroxyalkyl groups are exemplified by hydroxymethyl, dihydroxypropyl and the like.

The term "methine," as used herein, represents a =C(H)— group.

The term "nitro," as used herein, represents an —$NO_2$ group.

The terms "N-protecting group" or "nitrogen protecting group" as used herein, represent those groups intended to protect an amino group against undersirable reactions during synthetic procedures. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl and the like; arylalkyl groups such as benzyl, triphenylmethyl, benzyloxymethyl and the like and silyl groups such as trimethylsilyl and the like. Preferred N-protecting groups are formyl, acetyl, benzoyl, pivaloyl, t-butylacetyl, phenylsulfonyl, benzyl, t-butyloxycarbonyl (Boc) and benzyloxycarbonyl (Cbz).

The term "N-protected amino," as used herein, represents an amino group to which is attached an N-protecting or nitrogen-protecting group.

The term "N-protected aminoalkyl," as used herein, represents an alkyl group which is substituted by an N-protected amino group.

The term"O-protected carboxy," as used herein, represents an ester or amide group intended to protect a carboxy group against undersirable reactions during synthetic procedures. Additionally, a carboxy protecting group can be used as a prodrug whereby the carboxy protecting group can be readily cleaved in vivo, for example, by enzymatic hydrolysis, to release the biologically-active parent compound. Such carboxy protecting groups are well-known to those skilled in the art, having been extensively used in the protection of carboxyl groups in the penicillin and cephalosporin fields as described in U.S. Pat. Nos. 3,840,556 and 3,719,667, the disclosures of which are incorporated herein by reference. Representative carboxy protecting groups are $C_1$–$C_8$ loweralkyl (e.g., methyl, ethyl or t-butyl and the like); arylalkyl such as phenethyl or benzyl and substituted derivatives thereof such as alkoxybenzyl or nitrobenzyl groups and the like; arylalkenyl such as phenylethenyl and the like; aryl and substituted derivatives thereof such as 5-indanyl and the like; dialkylaminoalkyl such as dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl such as benzoyloxymethyl, benzoyloxyethyl and the like; arylalkylcarbonyloxyalkyl such as benzylcarbonyloxymethyl, 2-benzylcarbonyloxyethyl and the like; alkoxycarbonylalkyl or cycloalkyloxycarbonylalkyl such as methoxycarbonylmethyl, cyclohexyloxycarbonylmethyl, 1-methoxycarbonyl-1-ethyl and the like; alkoxycarbonyloxyalkyl or cycloalkyloxycarbonyloxyalkyl such as methoxycarbonyloxymethyl, t-butyloxycarbonyloxymethyl, 1-ethoxycarbonyloxy-1-ethyl, 1-cyclohexyloxycarbonyloxy-1-ethyl and the like; aryloxycarbonyloxyalkyl such as 2-(phenoxycarbonyloxy)ethyl, 2-(5-indanyloxycarbonyloxy)ethyl and the like; alkoxyalkylcarbonyloxyalkyl such as 2-(1-methoxy-2-methylpropan-2-oyloxy)ethyl and like; arylalkyloxycarbonyloxyalkyl such as 2-(benzyloxycarbonyloxy)ethyl and the like; arylalkenyloxycarbonyloxyalkyl such as 2-(3-phenylpropen-2-yloxycarbonyloxy)ethyl and the like; alkoxycarbonylaminoalkyl such as t-butyloxycarbonylaminomethyl and the like; alkylaminocarbonylaminoalkyl such as methylaminocarbonylaminomethyl and the like; alkanoylaminoalkyl such as acetylaminomethyl and the like; heterocycliccarbonyloxyalkyl such as 4-methylpiperazinylcarbonyloxymethyl and the like; dialkylaminocarbonylalkyl such as dimethylaminocarbonylmethyl, diethylaminocarbonylmethyl and the like; (5-(loweralkyl)-2-oxo-1,3-dioxolen-4-yl)alkyl such as (5-t-butyl-2-oxo-1,3-dioxolen-4-yl)methyl and the like; and (5-phenyl-2-oxo-1,3-dioxolen-4-yl)alkyl such as (5-phenyl-2-oxo-1,3-dioxolen-4-yl)methyl and the like.

The term "O-protected carboxyalkyl," as used herein, represents an alkyl group which is substituted by an O-protected carboxy group.

The term "parenterally," as used herein, refers to modes of administration which include intravenous, intramuscular, intraperitoneal, intrasternal, subcutaneous and intraarticular injection and infusion.

The term "pharmaceutically acceptable ester," as used herein, represents esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl group preferably has not more than 6 carbon atoms. Examples of particular esters includes formates, acetates, propionates, butyates, acrylates and ethylsuccinates.

The term "pharmaceutically acceptable salt," as use herein, represents those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The term "prodrug," as used herein, represents compounds which are rapidly transformed in vivo to the parent compound of formula (I), for example, by hydrolysis in blood. Higuchi et al., *Pro-drugs as Novel Delivery Systems*, v. 14 of the A.C.S. Symposium Series; Edward B. Roche, ed., *Bioreversible Carriers in Drug Design*, American Pharmaceutical Association and Pergamon Press (1987).

Asymmetric or chiral centers may exist in the compounds of the present invention. The present invention contemplates the various stereoisomers and mixtures thereof. Individual stereoisomers of compounds of the present invention are prepared synthetically from commercially available starting materials which contain asymmetric or chiral centers or by preparation of mixtures of enantiomeric compounds followed by resolution well-known to those of ordinary skill in the art. These methods of resolution are exemplified by (1) attachment of a racemic mixture of enantiomers, designated (±), to a chiral auxiliary, separation of the resulting diastereomers by recrystallization or chromatography and liberation of the optically pure product from the auxiliary or (2) direct separation of the mixture of optical enantiomers on chiral chromatographic columns. Enantiomers are designated herein by the symbols "R" or "S," depending on the configuration of substituents around the chiral carbon atom.

The preferred compounds are selected from formula (I), wherein $R_1$ is selected from the group consisting of a 2-$C_{1-8}$ alkoxy and a 3-$C_{1-8}$ alkoxy; $R_3$ is selected from the group consisting of structures (1), (7), (8) and (9); and wherein the ring formed by $R_4$ and $R_5$ is selected from the group consisting of (d), (e) and (f).

The more preferred compounds are selected from the preferred compounds, wherein $R_3$ is selected from the group consisting of substituted or unsubstituted benzothieno[3,2-d]pyrimidine-2,4(1H,3H)-dione, pyrido[2',3':4,5]thieno[3,2-d]pyrimidine-2,4(1H,3H)-dione, pyrido[3',2':4,5]thieno[3,2-d]pyrimidine-2,4(1H,3H)-dione, pyrazino[2',3':4,5]thieno[3,2-d]pyrimidine-2,4(1H,3H)-dione, 1H-isoindole-1,3(2H)-dione, 1,2-benzoisothiazol-3(2H)-one, 1,I-dioxide, 2H-1,4-benzoxazin-3(4H)-one and 2(1H)-quinolinone.

Even more preferred compounds are selected from the group consisting of:

(R)-3-[2-[3-(2-Methoxyphenyl)-1-pyrrolidinyl]ethyl]-[1] benzothieno[3,2-d]pyrimidine-2,4(1H,3H)-dione;

(R)-3-[4-[3-(2-Methoxyphenyl)-1-pyrrolidinyl]butyl]-[1]
benzothieno[3,2-d]pyrimidine-2,4(1H,3H)-dione;

(R)-3-[2-[3-(3-Methoxyphenyl)-1-pyrrolidinyl]ethyl]-[1]
benzothieno [3,2-d]pyrimidine-2,4(1H,3H)-dione;

(R)-3-[2-[3-(2-Methoxyphenyl)-1-pyrrolidinyl]ethyl]
pyrido[2',3':4,5]thieno[3,2-d]pyrimidine-2,4(1H,3H)-
dione;

(R)-3-[3-(2-Methoxyphenyl)-1-pyrrolidinyl]propyl]
pyrido[2',3':4,5]thieno[3,2-d]pyrimidine-2,4(1H,3H)-
dione;

(R)-3-[4-[3-(2-Methoxyphenyl)-1-pyrrolidinyl]butyl]
pyrido[2',3':4,5]thieno[3,2-d]pyrimidine-2,4(1H,3H)-
dione;

(R)-3-[5-[3-(2-Methoxyphenyl)-1-pyrrolidinyl]pentyl]
pyrido[2',3 ':4,5]thieno[3,2-d]pyrimidine-2,4(1H,3H)-
dione;

(R)-3-[4-[3-(2-Methoxyphenyl)-1-pyrrolidinyl]butyl]
pyrido [3',2':4,5]thieno[3,2-d]pyrimidine-2,4(1H,3H)-
dione;

(R)-3-[5-[3-(2-methoxyphenyl)-1-pyrrolidinyl]pentyl]
pyrido[3',2':4,5]thieno [3,2-d]pyrimidine-2,4(1H,3H)-
dione;

(R)-8-chloro-3-[4-[3-(2-methoxyphenyl)-1-pyrrolidinyl]
butyl]pyrido[2',3':4,5]thieno[3,2-d]pyrimidine-2,4(1H,
3H)-dione;

(R)-8-methoxy-3-[4-[3-(2-methoxyphenyl)-1-
pyrrolidinyl]butyl]pyrido[2',3':4,5]thieno[3,2-d]
pyrimidine-2,4(1H,3H)-dione;

(R)-2-[4-[3-(2-methoxyphenyl)-1-pyrrolidinyl]butyl]-
1H-isoindole-1,3(2H)-dione;

(R)-3-[4-[3-(2-Methoxyphenyl)-1-pyrrolidinyl]butyl]
pyrazino[2',3':4,5]thieno[3,2-d]pyrimidine-2,4(1H,
3H)-dione;

(R)-8-Chloro-3-[4-[3-(2-methoxyphenyl)-1-pyrrolidinyl]
butyl]pyrazino[2',3':4,5]thieno[3,2-d]pyrimidine-2,4
(1H,3H)-dione;

(R)-8-Methoxy-3-[4-[3-(2-methoxyphenyl)-1-
pyrrolidinyl]butyl]pyrazino[2 ',3':4,5]thieno[3,2-d]
pyrimidine-2,4(1H,3H)-dione;

(R)-8-phenyl-3-[4-[3-(2-methoxyphenyl)-1-pyrrolidinyl]
butyl]pyrazino[2',3':4,5]thieno[3,2-d]pyrimidine-2,4
(1H,3H)-dione;

(R)-2-[4-[3-(2-methoxyphenyl)-1-pyrrolidinyl]butyl]-1,
2-benzoisothiazol-3(2H)-one, 1,1-dioxide;

(R)-4-[4-[3-(2-methoxyphenyl)-1-pyrrolidinyl]butyl]-
2H-1,4-benzoxazin-3(4H)-one;

(R)-3,4-dihydro-1-[4-[3-(2-methoxyphenyl)-1-
pyrrolidinyl]butyl]-2(1H)-quinolinon;

(R)-3-[2-[3-(3-methoxyphenyl)-1-pyrrolidinyl]ethyl]
pyrido[2',3':4,5]thieno[3,2-d]pyrimidine-2,4(1H,3H)-
dione;

(R)-3-[3-[3-(3-methoxyphenyl)-1-pyrrolidinyl]propyl]
pyrido[2',3':4,5]thieno[3,2-d]pyrimidine-2,4(1H,3H)-
dione;

(R)-3-[4-[3-(3-methoxyphenyl)-1-pyrrolidinyl]butyl]
pyrido[2',3':4,5]thieno[3,2-d]pyrimidine-2,4(1H,3H)-
dione;

(R)-3-[2-[3-(3-methoxyphenyl)-1-pyrrolidinyl]ethyl]
pyrido[3 ',2':4,5]thieno[3,2-d]pyrimidine-2,4(1H,3H)-
dione;

(R)-3-[4-[3-(3-methoxyphenyl)-1-pyrrolidinyl]butyl]
pyrido[3',2':4,5]thieno[3,2-d]pyrimidine-2,4(1H,3H)-
dione;

(S)-3-[2-[3-(2-methoxyphenyl)-1-pyrrolidinyl]ethyl]-[1]
benzothieno[3,2-d]pyrimidine-2,4(1H,3H)-dione;

(S)-3-[2-[3-(3-methoxyphenyl)-1-pyrrolidinyl]ethyl]-[1]
benzothieno [3,2-d]pyrimidine-2,4(1H,3H)-dione;

(S)-3-[2-[3-(2-methoxyphenyl)-1-pyrrolidinyl]ethyl]
pyrido[2',3':4,5]thieno[3,2-d]pyrimidine-2,4(1H,3H)-
dione;

(S)-3-[3-[3-(2-methoxyphenyl)-1-pyrrolidinyl]propyl]
pyrido[2',3':4,5]thieno[3,2-d]pyrimidine-2,4(1H,3H)-
dione; and (S)-3-[4-[3-(2-methoxyphenyl)-1-pyrrolidinyl]butyl]
pyrido[2',3':4,5]thieno[3,2-d]pyrimidine-2,4(1H,3H)-
dione.

The most preferred compounds are selected from the group consisting of:

(R)-3-[4-[3-(2-Methoxyphenyl)-1-pyrrolidinyl]butyl]
pyrido[2',3':4,5]thieno[3,2-d]pyrimidine-2,4(1H,3H)-
dione;

(R)-3-[4-[3-(2-Methoxyphenyl)-1-pyrrolidinyl]butyl]
pyrido[3',2':4,5]thieno[3,2-d]pyrimidine-2,4(1H,3H)-
dione;

(R)-8-methoxy-3-[4-[3-(2-methoxyphenyl)-1-
pyrrolidinyl]butyl]pyrido[2',3':4,5]thieno[3,2-d]
pyrimidine-2,4(1H,3H)-dione;

(R)-2-[4-[3-(2-methoxyphenyl)-1-pyrrolidinyl]butyl]-
1H-isoindole-1,3(2H)-dione;

(R)-3-[4-[3-(2-Methoxyphenyl)-1-pyrrolidinyl]butyl]
pyrazino[2',3':4,5]thieno[3,2-d]pyrimidine-2,4(1H,
3H)-dione;

(R)-8-Chloro-3-[4-[3-(2-methoxyphenyl)-1-pyrrolidinyl]
butyl]pyrazino[2',3':4,5]thieno[3,2-d]pyrimidine-2,4
(1H,3H)-dione;

(R)-8-Methoxy-3-[4-[3-(2-methoxyphenyl)-1-
pyrrolidinyl]butyl]pyrazino[2',3':4,5]thieno[3,2-d]
pyrimidine-2,4(1H,3H)-dione;

(R)-8-phenyl-3-[4-[3-(2-methoxyphenyl)-1-pyrrolidinyl]
butyl]pyrazino[2',3':4,5]thieno[3,2-d]pyrimidine-2,4
(1H,3H)-dione; and (R)-2-[4-[3-(2-methoxyphenyl)-1-pyrrolidinyl]butyl]-1,
2-benzoisothiazol-3(2H)-one, 1,1-dioxide.

DETERMINATION OF BIOLOGICAL ACTIVITY

Representative compounds of the present invention were evaluated for their ability to displace prazosin from its adrenoreceptor.

In Vitro Binding Assays

For purposes of discussing $\alpha_1$ adrenoreceptor subtypes, the IUPHAR convention of using lower case letters to define molecular clones and upper case letters to indicate pharmacologically defined adrenoreceptors has been followed. Moreover, the newly recommended nomenclature for $\alpha_1$ receptor subtypes ($\alpha_{1a}$, $\alpha_{1b}$, $\alpha_{1d}$) has been used.

Representative compounds of the invention were evaluated for $\alpha$-adrenoreceptor binding affinity in vitro using [$^3$H]-prazosin as the radioligand and following four cloned $\alpha_1$ adrenoreceptors expressed in LTK cells: $\alpha_{1a}$ (rat), $\alpha_{1a}$ (bovine) $\alpha_{1b}$ (hampster) and $\alpha_{1d}$ (rat).

The cDNA clones encoding the $\alpha_1$ adrenoreceptors were obtained from TULCO (Triangle Universities Licensing Consortium, Research Triangle Park, N.C.) and inserted into the eukaryotic expression vector SnaB30. In this vector, expression of the adrenoreceptor gene is under the transcriptional control of an SV40 early promoter. Positive drug selection is provided by a neomycin-resistance gene. Mouse fibroblast cells (LTK) were transfected with the $\alpha_1$ expression plasmids and grown in Dulbecco's modified Eagle's medium (DMEM) containing 10% fetal calf serum and 30 μM G418. Stable G418-resistant parental lines were generated with successful expression of adrenoreceptor protein monitored using radioligand binding techniques. Stable single cell clones derived from the parental lines were screened in adrenoreceptor binding assays to identify clones having high adrenoreceptor density. Roller bottle cultures of the cloned lines were used to provide cell membranes for subsequent adrenoreceptor binding characterization studies. A cell line containing the SnaB30 vector expressing the human erythropoietin gene served as a negative control.

For adrenoreceptor binding assays, large scale membrane preparations were utilized in which 6 million cells were seeded into small (450 cm$^2$) Corning tissue culture roller bottles. DMEM (200 mL) containing 10% fetal calf serum and 300 μM G418 were added to each roller bottle. A 95% air/5% $CO_2$ gas mixture (sterile) was injected into each roller bottle prior to sealing, and the bottles were then incubated at 37° C. on a roller rack for 5 days. Cells were re-fed with fresh medium after 3 days in culture.

On the fifth day of culture, growth medium was removed from cells grown in roller bottles, and the cells were washed twice with PBS (Sigma, 120 mM NaCl, 2.7 mM KCl, 10 mM $Na_2HPO_4$—$NaH_2PO_4$, pH=7.4). Cells were detached from the roller bottles by incubating for 15 minutes at 37° C. in a Tris-EDTA solution (10 mM Tris, 100 mM NaCl, 1 mM EDTA, pH=7.4). The cell suspension from each roller bottle was decanted into tared centrifuge tubes and kept on ice. An aliquot of each cell suspension was generally taken for cell counting. Cells were centrifuged at 3000×G for 5 minutes at 2–4° C., washed with PBS and recentrifuged. The supernatant was decanted, and the pellet was weighed to determine the wet weight of cells. Cells were washed a final time in 40 vol 5 mM Tris-HCl, 5 mM EDTA, pH=7.7 and centrifuged at 40,000×G for 10 minutes. Cells were homogenized in of 50 mM Tris-HCl, 5 mM EDTA (pH=7.4) (10 mL) and diluted to 40 mL/tube. Homogenates were centrifuged at 40,000×G for 10 minutes. The supernatant was decanted and the pellets rehomogenized in 50 mM Tris-HCl (pH 7.4) and centrifuged as before. The supernatant was decanted and the homogenate was resuspended in 6.25 volumes (per gram wet weight) of 50 mM Tris-HCl and aliquots of the pooled homogenates frozen in liquid $N_2$ and stored at –70° C. until the time of assay.

Receptor binding assays for $\alpha_1$ adrenoreceptors were performed essentially as described by Greengrass et al., *Eur. J. Pharmacol.*, v. 55, 323–326 (1979). Briefly, plastic Bioblocks® (DBM Scientific, Valencia, Calif.) were incubated at 25° C. for 50 minutes with 500 μL of membrane homogenate (diluted with an additional 96 volumes (for cloned adrenoreceptors, 12 volumes for submaxillary gland) in 50 mM Tris-HCl buffer (pH =7.7 at the time of assay), 450 μL of [$^3$H]prazosin (0.2 nM final concentration, 75–85 Ci/mmole, DuPont—NEN Corp., Boston, Mass.) and 50 μL of either water (for total binding) or 10 μM phentolamine (final concentration, for non-specific binding)). Following equilibration, bound radioligand was separated from free on GF/B filters (presoaked in 0.5% polyethyleneimine) using either a Brandel or Packard cell harvester. Radioactivity was determined by standard liquid scintillation techniques. Data were analyzed as previously described by Hancock et al., *J. Receptor Res.*, v. 8, 23–46 (1988).

The results are shown in Table 1. These results show that the compounds of the invention bind to $\alpha_1$ adrenoreceptors and show varying degrees of specificity for the $\alpha_{1a}$ adrenoreceptor relative to $\alpha_{1b}$ and $\alpha_{1d}$ receptors.

TABLE 1

In Vitro Data for Binding to $\alpha_1$ Adrenoceptors

| Example | Radioligand Binding (Ki, nM) | | | |
|---|---|---|---|---|
| | $\alpha_{1a}$ (Rat) | $\alpha_{1a}$ (Bovine) | $\alpha_{1b}$ (Hamster) | $\alpha_{1d}$ (rat) |
| 1 | 1.80 | 0.13 | 0.94 | 0.82 |
| 2 | 0.18 | 0.02 | 0.62 | 0.03 |
| 3 | 34.01 | 5.95 | 59.71 | 20.04 |
| 4 | 2.61 | 0.83 | 1.52 | 2.38 |
| 5 | 2.05 | 1.25 | 9.68 | 2.25 |
| 6 | 0.12 | 0.05 | 1.77 | 0.22 |
| 7 | 2.11 | 0.18 | 4.86 | 2.13 |
| 8 | 0.12 | 0.06 | 1.76 | 0.09 |
| 9 | 3.30 | 0.32 | 7.38 | 2.35 |
| 10 | 0.22 | 0.05 | 1.18 | 0.06 |
| 11 | 0.67 | 0.11 | 1.79 | 0.12 |
| 12 | 0.32 | 0.06 | 0.96 | 0.28 |
| 13 | 0.21 | 0.07 | 2.99 | 0.36 |
| 14 | 0.22 | 0.09 | 5.90 | 0.47 |
| 15 | 0.26 | 0.06 | 2.37 | 0.15 |
| 16 | 1.61 | 0.09 | 11.8 | 0.64 |
| 17 | 0.13 | 0.03 | 1.10 | 0.22 |
| 18 | 0.46 | 0.21 | 1.02 | 0.66 |
| 19 | 0.57 | 0.15 | 0.93 | 0.23 |
| 20 | 46.34 | 11.98 | 194.42 | 69.43 |
| 21 | 27.27 | 8.00 | 70.68 | 92.16 |
| 22 | 5.11 | 1.52 | 18.36 | 11.48 |
| 23 | 134.40 | 26.96 | 331.26 | 86.41 |
| 24 | 7.37 | 2.81 | 20.03 | 5.19 |
| 25 | 9.33 | 1.67 | 5.61 | 3.86 |
| 26 | 6.79 | 1.24 | 10.68 | 3.04 |
| 27 | 14.42 | 2.46 | 15.72 | 8.48 |
| 28 | 25.82 | 10.27 | 88.63 | 27.84 |
| 29 | 1.98 | 0.69 | 4.02 | 2.02 |

PHARMACEUTICAL COMPOSITIONS

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection or for rectal administration.

The pharmaceutical compositions of this invention can be administered to humans and other animals orally, rectally, parenterally, intracisternally, intravaginally, intraperitoneally, topically (as by powders, ointments or drops), bucally or as an oral or nasal spray.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity may be maintained, for example, by the use of coating materials such as lecithin, by the maintenance of the required particle size in the case of dispersions and by the use of surfactants.

These compositions may also contain adjuvants such as preservative, wetting agents, emulsifying agents and dispersing agents. Prevention of the action of microorganisms may be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound is mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology,* Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of Compounds of this Invention

The compounds of this invention may be prepared by a variety of synthetic routes. Representative procedures are outlined in Schemes 1–4.

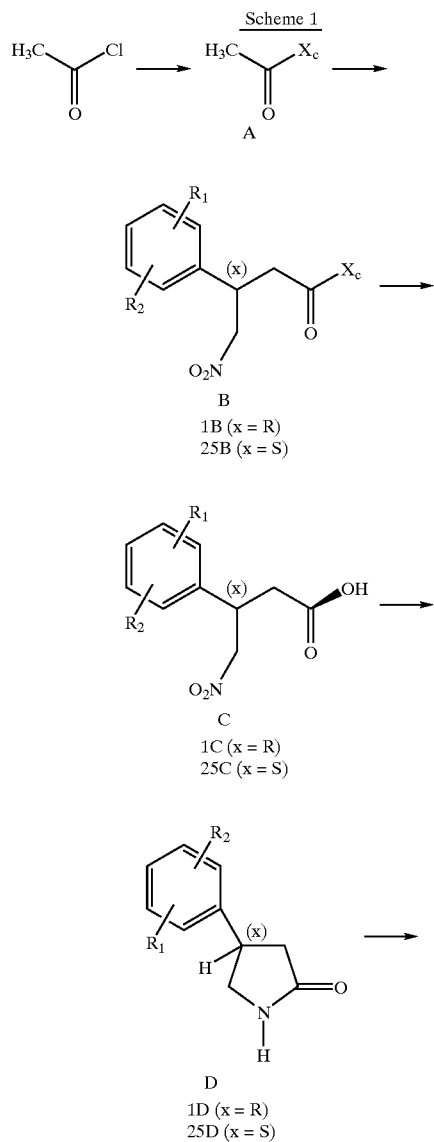

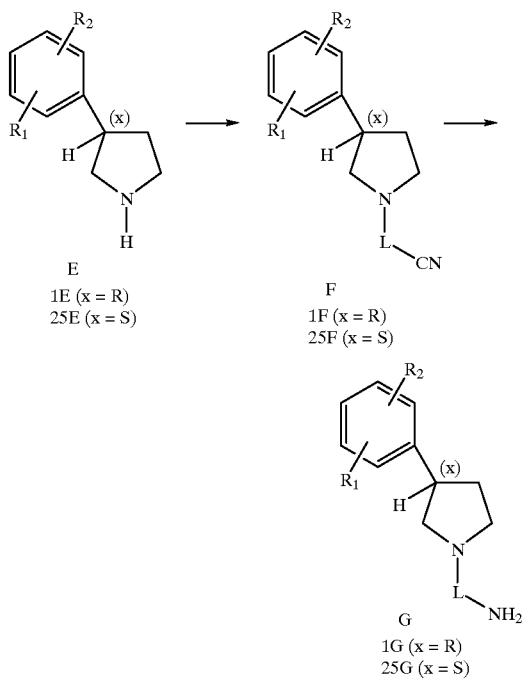

As shown in Scheme 1, acylation of chiral auxiliary $X_c$, preferably a chiral oxazolidinone, provided intermediate A. The disposition of substituents on the chiral auxiliary dictated the diastereofacial bias observed for the reaction of A with 4-trans-4-nitrovinylanisole or 2-trans-4-nitrovinylanisole and provided diastereomerically pure intermediate B. B was hydrolyzed with weak bese, preferably lithium hydroperoxide generated in situ from lithium hydroxide and 30% hydrogen peroxide to provide enantiomerically pure C. Catalytic reduction of C under a hydrogen atmosphere with a catalyst such as raney nickel or palladium on carbon and cyclization of the amino acid product with a base such as potassium tert-butoxide or sodium methoxide provided pyrrolidinone D. D was reduced with a hydride donating agent, preferably lithium aluminum hydride, to provide pyrroles E. E was converted to F with X-L-CN, where X is a leaving group, preferably bromide, and the varying length of L was incorporated by selection of the appropriate commercially available starting material. Reduction of F with lithium aluminum hydride, borane-THF or aluminum hydride, preferably a mixture of lithium aluminum hydride and aluminum hydride, provided amine G with varying chain length between the amino and pyrrole groups.

Scheme 2

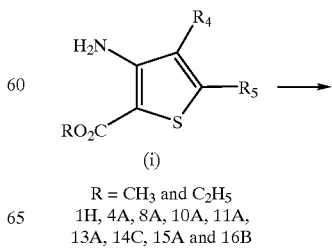

R = CH$_3$ and C$_2$H$_5$
1H, 4A, 8A, 10A, 11A, 13A, 14C, 15A and 16B

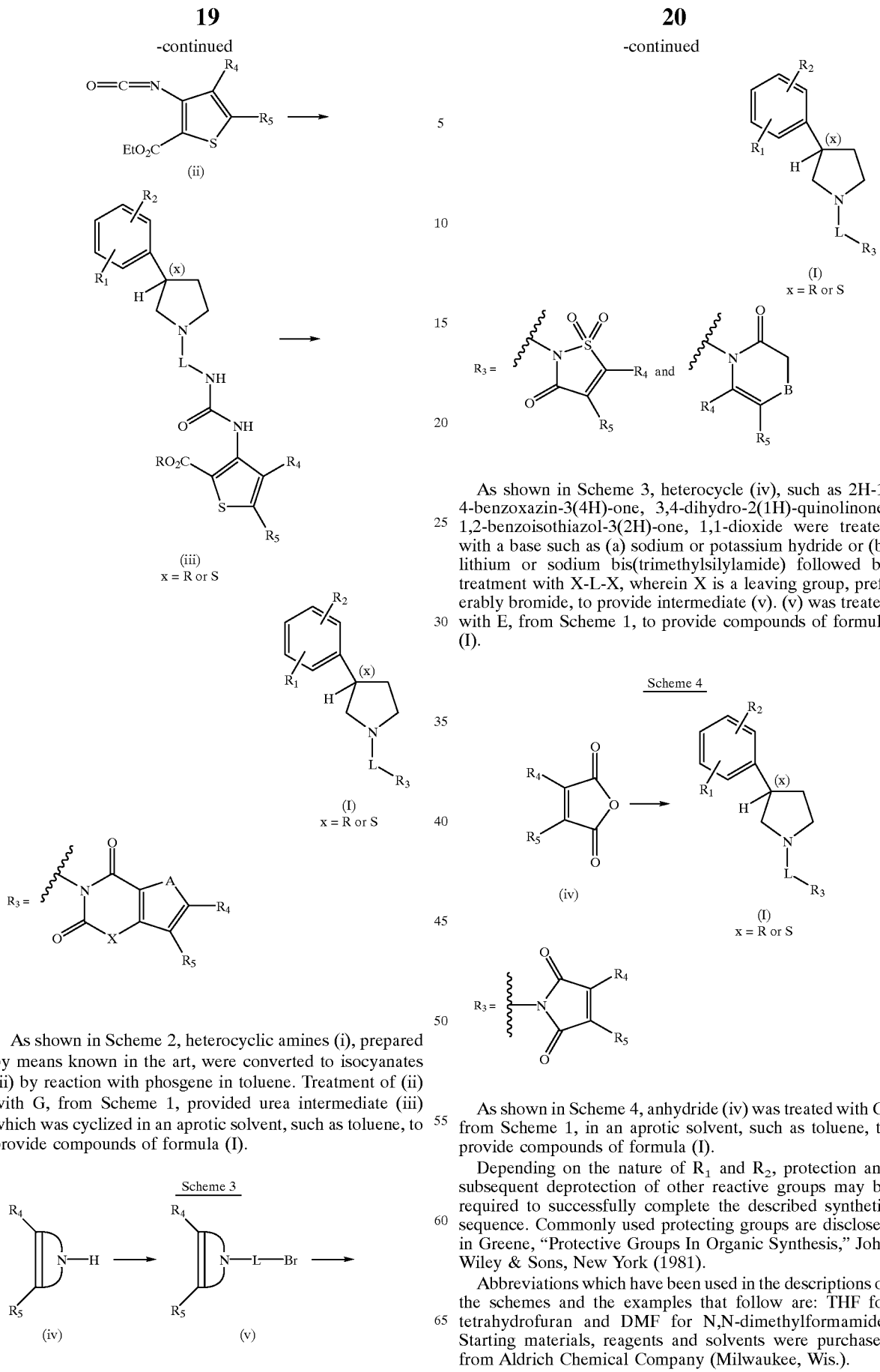

As shown in Scheme 2, heterocyclic amines (i), prepared by means known in the art, were converted to isocyanates (ii) by reaction with phosgene in toluene. Treatment of (ii) with G, from Scheme 1, provided urea intermediate (iii) which was cyclized in an aprotic solvent, such as toluene, to provide compounds of formula (I).

As shown in Scheme 3, heterocycle (iv), such as 2H-1,4-benzoxazin-3(4H)-one, 3,4-dihydro-2(1H)-quinolinone, 1,2-benzoisothiazol-3(2H)-one, 1,1-dioxide were treated with a base such as (a) sodium or potassium hydride or (b) lithium or sodium bis(trimethylsilylamide) followed by treatment with X-L-X, wherein X is a leaving group, preferably bromide, to provide intermediate (v). (v) was treated with E, from Scheme 1, to provide compounds of formula (I).

As shown in Scheme 4, anhydride (iv) was treated with G, from Scheme 1, in an aprotic solvent, such as toluene, to provide compounds of formula (I).

Depending on the nature of $R_1$ and $R_2$, protection and subsequent deprotection of other reactive groups may be required to successfully complete the described synthetic sequence. Commonly used protecting groups are disclosed in Greene, "Protective Groups In Organic Synthesis," John Wiley & Sons, New York (1981).

Abbreviations which have been used in the descriptions of the schemes and the examples that follow are: THF for tetrahydrofuran and DMF for N,N-dimethylformamide. Starting materials, reagents and solvents were purchased from Aldrich Chemical Company (Milwaukee, Wis.).

The invention is best illustrated by the examples recited below. However, these examples illustrate the preferred embodiment of the present invention, and do not limit the claims or the specification. The ordinary artisan will readily appreciate that changes and modifications to the specified embodiments can be made without departing from the scope and spirit of the invention. Finally, all citations herein are incorporated by reference.

EXAMPLE 1

(R)-3-[2-[3-(2-Methoxyphenyl)-1-pyrrolidinyl]ethyl]-[1]benzothieno[3,2-d]pyrimidine-2,4(1H,3H)-dione, Monohydrochloride

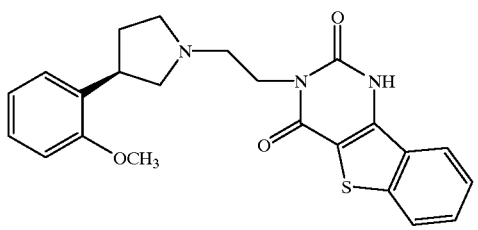

Example 1A (R)-3-Acetyl-4-(phenylmethyl)-2-oxazolidinone

The title compound was prepared with (R)-(+)-4-benzyl oxazolidinone according to the procedure in Synthesis (1), 1283–1285 (1996). MS (DCI/NH$_3$) m/e 220 (M+H)$^+$.

Example 1B (R,R)-3-[3-(2-Methoxyphenyl)-4-nitro-1-oxobutyl]-4-(phenylmethyl)-2-oxazolidinone A solution of Example 1A (2.4 g, 10.95 mmol) in THF (80 mL) was treated with sodium bis(trimethylsilyl)amide (2.0 g, 10.95 mmol) at −78° C., stirred for 1 hour, treated with 4-trans-4-nitrovinylanisole (1.96 g, 10.95 mmol) in THF (10 mL) at −78° C. via syringe, stirred for two hours then quenched with saturated aqueous ammonium chloride. The organic layer was diluted with ethyl acetate, washed sequentially with 1N HCl, water and brine, dried (MgSO$_4$) and concentrated. The residue was chromatographed on silica gel with 3:1 hexanes:ethyl acetete then crystallized from ethyl acetate/hexanes to provide the title compound. MS (DCI/NH$_3$) m/e 416 (M+NH$_4$)$^+$.

Example 1C (R)-2-Methoxy-β-(nitromethyl)benzenepropanoic Acid

A solution of Example 1B (1.70 g, 4.29 mmol) in 4:1 THF:water (15 mL) at 0° C. was treated sequentially with 30% hydrogen peroxide (1.95 mL, 17.17 mmol) and lithium hydroxide monohydrate (288 mg, 6.86 mmol), stirred for 3 hours, treated with sodium sulfite (288 mg, 6.86 mmol) in water (30 mL) and concentrated. The residue was extracted with methylene chloride, and the aqueous layer was cooled to 0° C. and acidified to pH 1 with 1M HCl then extracted with ethyl acetate. The extract was washed with brine, dried (MgSO$_4$) and concentrated, and the residue was chromatographed on silica gel with 99% (1:1 hexanes:ethyl acetate)/1% acetic acid to provide the title compound. MS (DCI/NH$_3$) m/e 257 (M+NH$_4$)$^+$.

Example 1D (R)-4-(2-Methoxyphenyl)-2-pyrrolidinone

A solution of Example 1C (670 mg, 2.8 mmol) in ethanol (12 mL) was treated with raney nickel (2 g), stirred under hydrogen (4 atm) at room temperature for 19 hours, filtered with and evaporated. The residue was taken up in 2.0M HCl/ethanol (600 mL), refluxed for 7 hours, cooled to room temperature and concentrated. This residue was dissolved in THF (900 mL) at 0° C., treated with potassium t-butoxide (355 mg, 3.2 mmol), stirred at ambient temperature overnight, treated with water and extracted with ethyl acetate. The extract was washed sequentially with 1N HCl, water and brine, dried (MgSO$_4$) and concentrated, and the residue was chromatographed on silica gel with 89:9:1 methylene chloride:methanol:concentrated ammonium hydroxide to provide the crude product which was crystallized from ethyl acetate/hexanes to provide the title compound.
MS (DCI/NH$_3$) m/e 192 (M+H)$^+$.

Example 1E (R)-3-(2-Methoxyphenyl)pyrrolidine Hydrochloride

A solution of Example 1D (202 mg, 1.1 mmol) in THF (20 mL) was treated with lithium aluminum hydride (80 mg, 2.1 mmol), refluxed for 12 hours, cooled, treated with Na$_2$SO$_4$.10H$_2$O (1.0 g), filtered through Celite® and concentrated. The residue was chromatographed on silica gel with 89:9:1 methylene chloride:methanol:concentrated ammonium hydroxide then treated with 1.0M HCl in ether (20 mL) to provide the title compound. MS (DCI/NH$_3$) m/e 178 (M+H)$^+$.

Example 1F (R)-3-(2-Methoxyphenyl)-1-pyrrolidineacetonitrile

A solution of Example 1E (150 mg, 0.85 mmol), bromoacetonitrile (78 μL, 0.940 mmol) and diisopropylethylamine (176 μL, 1.27 mmol) in acetonitrile (5 mL) was heated at 100° C. for 36 hours, cooled and concentrated. The residue was treated with 10% aqueous sodium carbonate and extracted with ethyl acetate. The ethyl acetate layer was washed with brine, dried (Na$_2$SO$_4$) and concentrated. Flash chromatography of the residue on silica gel with 1:1 hexane/ethyl acetate provided the title compound. MS (DCI/NH$_3$) m/e 217 (M+H)$^+$.

Example 1G (R)-3-(2-Methoxyphenyl)-1-pyrrolidineethanamine

A solution of Example 1F (1 g, 4.62 mmol) in THF (100 mL) was treated with lithium aluminum hydride (351 mg, 9.25 mmol), refluxed for 6 hours, cooled, treated with Na$_2$SO$_4$.10H$_2$O (2g), filtered through Celite® and concentrated. The residue was chromatographed on silica gel with 89:9:1 methylene chloride:methanol:concentrated ammonium hydroxide to provide the title compound. MS (DCI/NH$_3$) m/e 221 (M+H)$^+$.

Example 1H

Ethyl 3-aminobenzo[b]thiophene-2-carboxylate

The title compound was prepared according to the procedure in J. Org. Chem., v. 37(21), p. 3224 et seq. (1972).

Example 1I (R)-3-[2-[3-(2-Methoxyphenyl)-1-pyrrolidinyl]
ethyl]-[1]benzothieno[3,2-d]pyrimidine-2,4(1H,3H)-
dione Monohydrochloride A solution of Example 1H (664 mg, 3 mmol) and triethylamine (0.84 mL, 6 mmol) in THF (20 mL) was treated with 1.93M phosgene in toluene (1.7 mL, 3.3 mmol), stirred for 2 hours, treated with a solution of Example 1G (330 mg, 1.5 mmol) in toluene (50 mL), stirred for 4 hours, treated with 5% aqueous sodium bicarbonate and extracted with methylene chloride. The extract was dried ($Na_2SO_4$) and concentrated, and the residue was dissolved in toluene, refluxed for 18 hours, cooled and filtered. The filtrate was treated with ethanol saturated with HCl, triturated with diethyl ether and filtered to provide the title compound. mp 169–173° C.; $[\alpha]_D^{23}$=+3.7° (c 0.004, MeOH); $^1$H NMR (300 MHz, $CD_3OD$) δ 2.19–2.55 (m, 2H), 3.30 (m, 1H), 3.55 (m, 1H), 3.67 (t, 3H), 3.78 (m, 1H), 3.90 (s, 3H), 4.00 (m, 1H), 4.16 (q, 1H), 4.48 (t, 2H), 6.98 (m, 2H), 7.28 (m, 2H), 7.60 (m, 2H), 8.01 (d, 1H), 8.21 (d, 1H); MS ($DCI/NH_3$) m/e 422 $(M+H)^+$; Anal. calc'd for $C_{23}H_{23}N_3O_3S \cdot 1.0$ HCl: C, 60.32, H, 5.28, N, 9.18,. Found: C, 60.82, H, 5.36, N, 9.22.

EXAMPLE 2

(R)-3-[4-[3-(2-Methoxyphenyl)-1-pyrrolidinyl]
butyl]-[1]benzothieno[3,2-d]pyrimidine-2,4(1H,3H)-
dione Monohydrochloride

Example 2A (R)-3-(2-Methoxyphenyl)-1-pyrrolidinebutanenitrile

The title compound was prepared from Example 1E and 4-bromobutyronitrile according to the procedure in Example 1F. MS ($DCI/NH_3$) m/e 245 $(M+H)^+$.

Example 2B (R)-3-(2-Methoxyphenyl)-1-pyrrolidinebutanamine

The title compound was prepared from Example 2A according to the procedure in Example 1G. MS ($DCI/NH_3$) m/e 249 $(M+H)^+$.

Example 2C (R)-3-[4-[3-(2-Methoxyphenyl)-1-pyrrolidinyl]
butyl]-[1]benzothieno[3,2-d]pyrimidine-2,4(1H,3H)-
dione Monohydrochloride The title compound was prepared from Example 2B and Example 1H according to the procedure in Example 1I. mp >250° C.; $[\alpha]_D^{23}$=+1.58° (c 0.002, MeOH); $^1$H NMR (300 MHz, $CD_3OD$) δ 2.19–2.55 (m, 2H), 3.30 (m, 1H), 3.55 (m, 1H), 3.67 (t, 3H), 3.78 (m, 1H), 3.90 (s, 3H), 4.00 (m, 1H), 4.16 (q, 1H), 4.48 (t, 2H), 6.98 (m, 2H), 7.28 (m, 2H), 7.60 (m, 2H), 8.01 (d, 1H), 8.21 (d, 1H); MS ($DCI/NH_3$) m/e 422 $(M+H)^+$; Anal. calcd for $C_{23}H_{23}N_3O_3S \cdot 1.7$HCl: C, 57.14; H, 5.15; N, 8.69. Found: C, 57.02; H, 5.29; N, 8.43.

EXAMPLE 3

(R)-3-[2-[3-(3-Methoxyphenyl)-1-pyrrolidinyl]
ethyl]-[1]benzothieno[3,2-d]pyrimidine-2,4(1H,3H)-
dione Monohydrochloride

Example 3A (R,R)-3-[3-(3-Methoxyphenyl)-4-nitro-1-oxobutyl]-
4-(phenylmethyl)-2-oxazolidinone The title compound was prepared from Example 1A according to the procedure in Example 1B but substituting 2-trans-2-nitrovinylanisole for 4-trans-4-nitrovinylanisole. MS ($DCI/NH_3$) m/e 416 $(M+NH_4)^+$.

Example 3B (R)-3-Methoxy-β-(nitromethyl)benzenepropanoic Acid

The title compound was prepared from Example 3A according to the procedure in Example 1 C. MS ($DCI/NH_3$) m/e 257 $(M+NH_4)^+$.

Example 3C (R)-4-(3-Methoxyphenyl)-2-pyrrolidinone

The title compound was prepared from Example 3B according to the procedure in Example 1D. MS ($DCI/NH_3$) m/e 192 $(M+NH_4)^+$.

Example 3D (R)-3-(3-Methoxyphenyl)pyrrolidine

The title compound was prepared from Example 3C according to the procedure in Example 1E. MS ($DCI/NH_3$) m/e 178 $(M+H)^+$.

Example 3E (R)-3-(3-Methoxyphenyl)-1-pyrrolidineacetonitrile

The title compound was prepared from Example 3D according to the procedure in Example 1F. MS ($DCI/NH_3$) m/e 217 $(M+H)^+$.

Example 3F (R)-3-(3-Methoxyphenyl)-1-pyrrolidineethanamine

The title compound was prepared from Example 3E according to the procedure in Example 1G. MS ($DCI/NH_3$) m/e 221 $(M+H)^+$.

Example 3G (R)-3-[2-[3-(3-Methoxyphenyl)-1-pyrrolidinyl]
ethyl]-[1]benzothieno[3,2-d]pyrimidine-2,4(1H,3H)-
dione Monohydrochloride The title compound was prepared from Examples 3F and 1H according to the procedure in Example 1I. mp >250° C.; $[\alpha]_D^{23}$=+1.47° (c 0.002, MeOH); $^1$H NMR (300 MHz, $CD_3OD$) δ 2.19–2.55 (m, 2H), 3.30 (m, 1H), 3.55 (m, 1H), 3.67 (t, 3H), 3.78 (m, 1H), 3.90 (s, 3H), 4.00 (m, 1H), 4.16 (q, 1H), 4.48 (t, 2H), 6.98 (m, 2H), 7.28 (m, 2H), 7.60 (m, 2H), 8.01 (d, 1H), 8.21 (d, 1H); MS ($DCI/NH_3$) m/e 422 $(M+H)^+$; Anal. calc'd for $C_{23}H_{23}N_3O_3S \cdot 1.5$HCl: C, 57.14; H, 5.15; N, 8.69. Found: C, 57.02; H, 5.29; N, 8.43.

EXAMPLE 4

(R)-3-[2-[3-(2-Methoxyphenyl)-1-pyrrolidinyl]ethyl]pyrido[2',3':4.5]thieno[3,2-d]pyrimidine-2,4(1H,3H)-dione Dihydrochloride

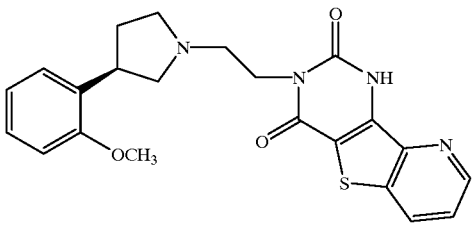

Example 4A

Ethyl 3-aminothieno[3,2-b]pyridine-2-carboxylate

The title compound was prepared according to the procedure in *J. Heterocyclic Chem.*, v. 24, p. 85 (1987).

Example 4B (R)-3-[2-[3-(2-Methoxyphenyl)-1-pyrrolidinyl]ethyl]pyrido[2',3':4,5]thieno[3,2-d]pyrimidine-2,4(1H,3H)-dione bis(hydrochloride) Salt The title compound was prepared from Examples 4A and 1G according to the procedure in Example 11. mp 195–198° C.; $[\alpha]_D^{23}$=+2.2° (c 0.003, MeOH); $^1$H NMR (300 MHz, CD$_3$OD) δ 2.19–2.55 (m, 2H), 3.30 (m, 1H), 3.55 (m, 1H), 3.67 (t, 2H), 3.78 (m, 1H), 3.86 (s, 1.5H), 3.91 (s, 1.5H), 4.00 (m, 1H), 4.16 (q, 1H), 4.48 (t, 2H), 6.95 (m, 1H), 7.02 (d, 1H), 7.25 (q, 2H), 7.61 (q, 1H), 8.50 (d, 1H), 8.79 (d, 1H), 8.81 (d, 1H); MS (DCI/NH$_3$) m/e 423 (M+H)$^+$; Anal. calc'd for C$_{22}$H$_{22}$N$_4$O$_3$S.3.0 HCl: C, 49.68; H, 4.74; N, 10.53. Found: C, 49.37; H; 4.93; N, 10.69.

EXAMPLE 5

(R)-3-[3-[3-(2-Methoxyphenyl)-1-pyrrolidinyl]propyl]pyrido[2',3':4,5]thieno[3,2-d]pyrimidine-2,4(1H,3H)-dione Dihydrochloride

Example 5A (R)-3-(2-Methoxyphenyl)-1-pyrrolidinepropanenitrile

The title compound was prepared from Example 1E and 3-bromopropionitrile according to the procedure in Example 1F. MS (DCI/NH$_3$) m/e 231 (M+H)$^+$.

Example 5B (R)-3-(2-Methoxyphenyl)pyrrolidinyl-1-propanamine

The title compound was prepared from Example 5A according to the procedure in Example 1G. MS (DCI/NH$_3$) m/e 235 (M+H)$^+$.

Example 5C (R)-3-[3-[3-(2-Methoxyphenyl)-1-pyrrolidinyl]propyl]pyrido[2',3':4.5]thieno[3,2-d]pyrimidine-2,4(1H,3H)-dione, Dihydrochloride The title compound was prepared from Examples 5B and 4A according to the procedure in Example 11. mp >250° C., $[\alpha]_D^{23}$=−5.7° (c 0.007, MeOH); $^1$H NMR (300 MHz, CDCl$_3$) δ 2.21 (m, 2H), 2.30–2.57 (m, 2H), 3.39 (t, 3H), 3.58–3.82 (m, 3H), 3.84 (s, 1.5H), 3.91 (s, 1.5H), 3.99 (m, 1H), 4.21 (m, 2H), 6.99 (m, 1H), 7.02 (d, 1H), 7.23 (m, 2H), 7.60 (q, 1H), 8.50 (d, 1H), 8.81 (d, 1H); MS (DCI/NH$_3$) m/e 437 (M+H)$^+$; Anal. calc'd for C$_{23}$H$_{24}$N$_4$O$_3$S.2.5 HCl 1.0 CH$_3$OH . C, 51.50; H, 5.49; N, 10.01. Found: C, 51.23; H, 5.23; N, 9.72.

EXAMPLE 6

(R)-3-[4-[3-(2-Methoxyphenyl)-1-pyrrolidinyl]butyl]pyrido[2',3':4,5]thieno[3,2-d]pyrimidine-2,4(1H,3H)-dione Dihydrochloride

Example 6A (R)-3-[4-[3-(2-Methoxyphenyl)-1-pyrrolidinyl]butyl]pyrido[2',3':4,5]thieno[3,2-d]pyrimidine-2,4(1H,3H)-dione, Dihydrochloride The title compound was prepared from Examples 2B and 4A according to the procedure in Example 1I. mp 230–233° C.; $[\alpha]_D^{23}$=+11.5° (c 0.019, MeOH); $^1$H NMR (300 MHz, CD$_3$OD) δ 1.82 (bs, 4H), 2.18 (m, 2H), 3.38 (m, 3H), 3.62 (m, 2H), 3.78 (m, 2H), 3.90 (s, 3H), 3.95 (m, 1H), 4.15 (t, 2H), 6.95 (t, 1H), 7.02 (d, 1H), 7.28 (m, 2H), 7.60 (q, 1H), 8.45 (d, 0.5H), 8.46 (d, 0.5H), 8.81 (d, 0.5H), 8.82 (d, 0.5H). MS (DCI/NH$_3$) m/e 451 (M+H)$^+$; Anal. calc'd for C$_{24}$H$_{26}$N$_4$O$_3$S.2.1HCl.MeOH: C, 55.07; H, 5.39; N, 10.70. Found: C, 54.51; H, 5.37; N, 10.59.

EXAMPLE 7

(R)-3-[5-[3-(2-Methoxyphenyl)-1-pyrrolidinyl]pentyl]pyrido[2',3':4,5]thieno[3,2-d]pyrimidine-2,4(1H,3H)-dione, Dihydrochloride

Example 7A (R)-3-(2-Methoxyphenyl)-1-pyrrolidinepentanenitrile

The title compound was prepared from Example 1E and 5-bromovaleronitrile according to the procedure in Example 1F. MS (DCI/NH$_3$) m/e 259 (M+H)$^+$.

Example 7B (R)-3-(2-Methoxyphenyl)-1-pyrrolidinylpentanamine

The title compound was prepared from Example 7A according to the procedure in Example 1G. MS (DCI/NH$_3$) m/e 263 (M+H)$^+$.

Example 7C (R)-3-[5-[3-(2-methoxyphenyl)-1-pyrrolidinyl]pentyl]pyrido[2',3':4,5]thieno[3,2-d]pyrimidine-2,4(1H,3H)-dione, Dihydrochloride The title compound was prepared from Examples 7B and 4A according to the procedure in Example 1I. mp >250° C.; $[\alpha]_D^{23}$=+4.5° (c 0.002, MeOH); $^1$H NMR (CD$_3$OD) δ 1.51 (m, 2H), 1.70 (m, 2H), 1.82 (m, 2H), 2.18 (m, 2H), 3.38 (m, 3H), 3.62 (m, 2H), 3.78 (m, 2H), 3.90 (s, 3H), 3.95 (m, 1H), 4.15 (t, 2H), 6.95 (t, 1H), 7.02 (d, 1H), 7.28 (m, 2H), 7.60 (q, 1H), 8.45 (d, 0.5H), 8.46 (d, 0.5H), 8.81 (d, 0.5H), 8.82 (d, 0.5H); MS (DCI/NH$_3$) m/e 467 (M+H)$^+$; Anal. calc'd for $C_{25}H_{30}N_4O_3S \cdot 2.5 \ HCl \cdot 0.7C_4H_8O_2$: C, 53.91; H, 6.20, N; 9.05. Found: C, 53.86; H, 6.38; N, 8.94.

EXAMPLE 8

(R)-3-[4-[3-(2-Methoxyphenyl)-1-pyrrolidinyl]butyl] pyrido[3',2':4,5]thieno[3,2-d]pyrimidine-2,4(1H,3H)-dione, Dihydrochloride

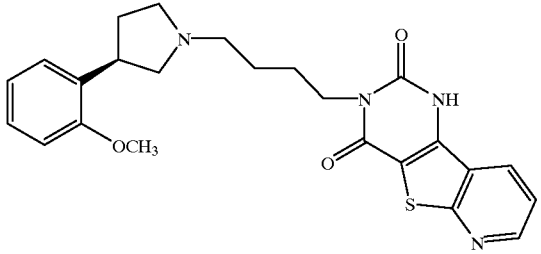

Example 8A

Ethyl 3-aminothieno[2,3-b]pyridine-2-carboxylate

The title compound was prepared by the procedure in *J. Heterocyclic Chem.*, v. 24, p. 85 (1987).

Example 8B (R)-3-[4-[3-(2-Methoxyphenyl)-1-pyrrolidinyl]butyl] pyrido[3',2':4,5]thieno[3,2-d]pyrimidine-2,4(1H,3H)-dione, dihydrochloride The title compound was prepared from Examples 8A and 2B according to the procedure in Example 11. mp 155–158° C.; $[\alpha]_D^{23}=-0.3°$ (c 0.008, MeOH); $^1$H NMR (CD$_3$OD) δ 1.82 (bs, 4H), 2.18 (m, 2H), 3.38 (m, 3H), 3.62 (m, 2H), 3.78 (m, 2H), 3.90 (s, 3H), 3.95 (m, 1H), 4.15 (t, 2H), 6.96 (t, 1H), 7.02 (d, 1H), 7.24 (m, 2H), 7.59 (q, 1H), 8.56 (d, 0.5H), 8.57 (d, 0.5H), 8.78 (d, 0.5H), 8.79 (d, 0.5H); MS (DCI/NH$_3$) m/e 451 (M+H)$^+$; Anal. calc'd for $C_{24}H_{26}N_4O_3S \cdot 1.0 \ HCl \cdot 0.5C_4H_{10}O_2 \ 0.1H_2O$: C, 58.20; H, 6.10; N, 10.44. Found: C, 58.13; H, 5.83; N, 10.16.

EXAMPLE 9

(R)-3-[5-[3-(2-methoxyphenyl)-1-pyrrolidinyl] pentyl]pyrido[3',2':4,5]thieno[3,2-d]pyrimidine-2,4(1H,3H)-dione, Dihydrochloride

Example 9A (R)-3-[5-[3-(2-methoxyphenyl)-1-pyrrolidinyl] pentyl]pyrido[3',2':4.5]thieno[3,2-d]pyrimidine-2,4(1H,3H)-dione, Dihydrochloride The title compound was prepared from Examples 7B and 8A according to the procedure in Example 11. mp 115–118° C.; $[\alpha]_D^{23}=+1.0°$ (c 0.005, MeOH); $^1$H NMR (CD$_3$OD) δ 1.51 (m, 2H), 1.70 (m, 2H), 1.82 (m, 2H), 2.18 (m, 2H), 3.38 (m, 3H), 3.62 (m, 2H), 3.78 (m, 2H), 3.90 (s, 3H), 3.95 (m, 1H), 4.15 (t, 2H), 6.96 (t, 1H), 7.02 (d, 1H), 7.24 (m, 2H), 7.59 (q, 1H), 8.56 (d, 0.5H), 8.57 (d, 0.5H), 8.78 (d, 0.5H), 8.79 (d, 0.5H). MS (DCI/NH$_3$) m/e 467 (M+H)$^+$; Anal. calc'd for $C_{25}H_{30}N_4O_3S \cdot 2.3 \ HCl \cdot 1 \ C_4H_8O_2$: C, 53.97; H, 6.57; N, 8.48. Found: C, 53.96; H, 6.72; N, 8.47.

EXAMPLE 10

(R)-8-chloro-3-[4-[3-(2-methoxyphenyl)-1-pyrrolidinyl]butyl]pyrido[2',3':4.5]thieno[3,2-d] pyrimidine-2,4(1H,3H)-dione, Dihydrochloride

Example 10A

Methyl 3-amino-7-chlorothieno[3,2-b]pyridine-2-carboxylate

A solution of 3-chloro-2-cyanopyridine (40 g, 0.29 mol) in acetic acid (500 mL) was treated dropwise with hydrogen peroxide (30%, 52 g, 0.45 mol), stirred at 90° C. for 18 hours, cooled to 25° C., treated dropwise with a solution of sodium sulfite (57 g, 0.45 mol) in water, concentrated to remove the bulk of the acetic acid and partitioned between 1M NaOH and methylene chloride. The methylene chloride layer was dried (MgSO$_4$) and concentrated, and the residue was recrystallized from ethyl acetate to provide 23 g of 3-chloro-2-cyanopyridine—N-oxide, a portion of which (12.2 g, 79 mmol) was dissolved in DMF (160 mL) cooled to 0° C., treated sequentially with ethyl thioglycolate (7.1 mL, 79 mmol) and portionwise with sodium methoxide (8.5 g, 160 mmol), stirred for 1 hour and poured onto ice. The resulting solid was collected by filtration, washed with water, dissolved in methylene chloride, dried (MgSO$_4$), concentrated and recrystallized from ethyl acetate to provide 10.6 g of methyl 3-amino-thieno[3,2-b]pyridine-4-oxide carboxylate, a portion of which (10.6 g, 47 mmol) was mixed with phosphorous oxychloride (100 mL), heated to 80° C. for 30 minutes, concentrated and partitioned between methylene chloride and 5% aqueous NaHCO$_3$ solution. The methylene chloride layer was dried (MgSO$_4$) and concentrated, and the residue was chromatographed on silica gel with 5:1 hexanes/ethyl acetate to first provide methyl 3-amino-5-chloro-thieno[3,2-b]pyridine-2-carboxylate followed by the title compound. MS (DCI/NH$_3$) m/e 243 (M+H)$^+$.

Example 10B (R)-8-chloro-3-[4-[3-(2-methoxyphenyl)-1-pyrrolidinyl]butyl]pyrido[2',3':4,5]thieno[3,2-d] pyrimidine-2,4(1H,3H)-dione, Dihydrochloride The title compound was prepared from Examples 10A and 2B according to the procedure in Example 1I. mp 1 10–120° C.; $[\alpha]_D^{23}=-4.00°$ (c 0.25, CH$_2$Cl$_2$); $^1$H NMR (300 MHz, CD$_3$OD) δ 1.84–1.92 (m, 4H), 2.20–2.44 (m, 2H), 3.17–3.44 (m, 4H), 3.59–3.63 (m, 1H), 3.75–3.95 (m, 5H), 4.07–4.12 (m, 2H), 6.94 (t, 1H), 7.02 (d, 1H), 7.22–7.31 (m, 2H), 7.62 (d, 1H), 8.46 (d, 1H); MS (DCI/NH$_3$) m/e 485.00 (M+H)$^+$; Anal. calc'd. for $C_{24}H_{25}N_4O_3SCl \cdot 0.2HCl \cdot 0.8H_2O$: C, 52.89; H, 5.15; N, 10.28. Found: C, 52.92; H, 5.14; N, 10.06.

EXAMPLE 11

(R)-8-methoxy-3-[4-[3-(2-methoxyphenyl)-1-pyrrolidinyl]butyl]pyrido-[2',3':4,5]thieno[3,2-d] pyrimidine-2,4(1H,3H)-dione, Dihydrochloride

Example 11A

Methyl 3-Amino-5-methoxy-thieno[3,2-b]pyridine-2-carboxylate

A solution of methyl 3-amino-5-chloro-thieno[3,2-b] pyridine-2-carboxylate, prepared according to the procedure in Example 10A (5 g, 21 mmol) and sodium methoxide (4.5 g, 82 mmol) in methanol (150 mL) was refluxed for 18 hours, concentrated and partitioned between ethyl acetate and saturated aqueous NaHCO$_3$. The ethyl acetate layer was dried (MgSO$_4$) and concentrated, and the residue was chromatographed on silica gel with 5:1 hexanes/ethyl acetate to provide the title compound. MS (DCI/NH$_3$) m/e 239 (M+H)$^+$.

Example 11B (R)-8-methoxy-3-[4-[3-(2-methoxyphenyl)-1-pyrrolidinyl]butyl]pyrido-[2',3':4,5]thieno[3,2-d] pyrimidine-2,4(1H,3H)-dione, Dihydrochloride The title compound was prepared from Examples 11A and 2B according to the procedure in Example 11. mp 176–180°

C.; $[\alpha]_D^{23}$=+10.67 (c 0.30, $CH_2Cl_2$); $^1$H NMR ($CD_3OD$) δ 1.83–1.90 (m, 4H), 2.21–2.44 (m, 2H), 3.21–3.42 (m, 4H), 3.60–3.63 (m, 1H), 3.73–3.95 (m, 5H), 4.07 (s, 3H), 4.11–4.15 (m, 2H), 6.97 (tt, 1H), 7.02–7.05 (m, 2H), 7.22–7.32 (m, 2H), 8.24 (d, 1H); MS (DCI/$NH_3$) m/e 481 $(M+H)^+$; Anal. calc'd for $C_{25}H_{28}N_4O_4S$.033 HCl: C, 61.09; H, 5.80; N, 11.40. Found: C, 60.98; H, 5.73; N, 11.47.

EXAMPLE 12

(R)-2-[4-[3-(2-methoxyphenyl)-1-pyrrolidinyl]butyl]-1H-isoindole-1,3(2H)-dione, Monohydrochloride

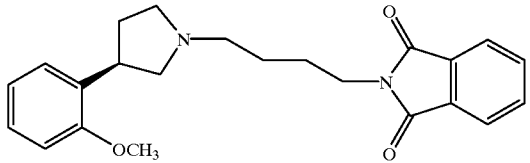

A solution of Example 2B (150 mg, 0.60 mmol) and phthalic anhydride (90 mg, 0.60 mmol) in toluene (20 mL) was refluxed for 18 hours, cooled to ambient temperature, washed with saturated aqueous $NaHCO_3$, dried ($MgSO_4$), concentrated and purified according to the procedure in Example 1I to provide the title compound. mp >200° C.; [α]=–6.2° (c 0.027, $^i$PrOH); $^1$H NMR (300 MHz, $CD_3OD$) δ 1.82 (br, 4H), 2.18 (m, 2H) 3.38 (m, 3H), 3.62 (m, 2H), 3.78 (m, 2H), 3.90 (s, 3H), 3.95 (m, 1H), 4.15 (t, 2H), 6.90 (t, 1H), 6.98 (d, 1H), 7.20 (m, 2H), 7.8 (m, 4H); MS (DCI/$NH_3$) m/e 379 $(M+H)^+$; Anal. calc'd. for $C_{23}H_{26}N_2O_3$.1.3HCl: C, 64.89; H, 6.46; N, 6.58. Found: C, 64.87; H, 6.48; N, 6.52.

EXAMPLE 13

(R)-3-[4-[3-(2-Methoxyphenyl)-1-pyrrolidinyl]butyl]pyrazino[2',3':4,5]thieno[3,2-d]pyrimidine-2,4(1H,3H)-dione, Dihydrochloride

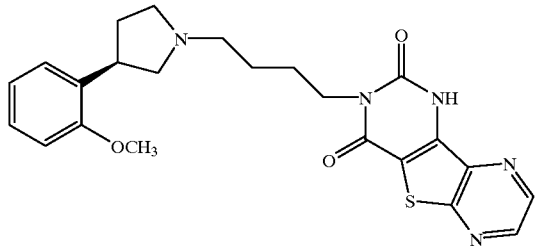

Example 13A

Ethyl 7-amino-thieno[2,3-b]pyrazine-6-carboxylate

The title compound was prepared by the method in J. Het. Chem., v. 12, p. 513 (1975).

Example 13B (R)-3-[4-[3-(2-Methoxyphenyl)-1-pyrrolidinyl]butyl]pyrazino[2',3':4,5]thieno[3,2-d]pyrimidine-2,4(1H,3H)-dione, Dihydrochloride The title compound was prepared from Examples 13A and 2B according to the procedure in Example 1I. mp 155–158° C.; $[\alpha]_D^{23}$=–2.0° (c 0.001, MeOH); $^1$H NMR ($CD_3OD$) δ 1.82 (bs, 4H), 2.18 (m, 2H), 3.38 (m, 3H), 3.62 (m, 2H), 3.78 (m, 2H), 3.90 (s, 3H), 3.95 (m, 1H), 4.15 (t, 2H), 6.90 (t, 1H), 6.98 (d, 1H), 7.20 (m, 2H), 8.70 (d, 1H), 8.78 (d, 1H); MS (DCI/$NH_3$) m/e 442 $(M+H)^+$; Anal. calc'd for $C_{23}H_{25}N_5O_3S$.2 HCl: C, 52.67, H, 5.19, N, 13.35. Found: C, 54.98; H, 5.54; N, 13.07.

EXAMPLE 14

(R)-8-Chloro-3-[4-[3-(2-methoxyphenyl)-1-pyrrolidinyl]butyl]pyrazino[2',3':4,5]thieno[3,2-d]pyrimidine-2,4(1H,3H)-dione, Dihydrochloride

Example 14A

2-Chloro-3-cyanopyrazine, 4-oxide

A solution of 2-chloro-3-cyanopyrazine (5.00 g, 35.94 mmol) in concentrated $H_2SO_4$ (35 mL) at 0° C. was treated portionwise with $K_2S_2O_8$ (11.65 g, 43.95 mmol), warmed to room temperature, stirred for 24 hours and partitioned between chloroform and ice water. The separated aqueous phase was extracted with chloroform, and the combined organic extracts were washed with water, saturated $NaHCO_3$ and brine, dried ($MgSO_4$) and concentrated to provide the title compound. MS (DCI/$NH_3$) m/e 173 $(M+NH_4)^+$.

Example 14B

Ethyl 7-aminothieno[2,3-b]pyrazine-6-carboxylate, 1-oxide

A solution of Example 14A (2.90 g, 18.64 mmol) in DMF (100 mL) was treated with ethyl thioglycolate (2.24 g, 18.64 mmol), cooled to 0° C., treated with solid sodium ethoxide (2.54 g, 37.29 mmol) warmed to room temperature, stirred for 13 hours and partitioned between ethyl acetate and brine. The layers were separated, and the aqueous phase was extracted with ethyl acetate. The combined organic extracts were washed with water and brine, dried ($MgSO_4$) and concentrated to a yellow solid which was purified by column chromatography on silica gel with 2:1 then 1:1 hexanes/ethyl acetate to provide 3.50 g of the title compound as a yellow solid. MS (DCI/$NH_3$) m/e 240 $(M+H)^+$ and 257 $(M+NH_4)^+$.

Example 14C

Ethyl-7-amino-2-chloro-thieno [2,3-b]pyrazine-6-carboxylate

A solution of Example 14B (0.88 g, 3.68 mmol) in $POCl_3$ (50 mL) was heated to 95° C. for 3 hours, concentrated and partitioned between ethyl acetate and water. The aqueous phase was extracted with ethyl acetate, and the combined organic extracts were washed sequentially with water, saturated aqueous $NaHCO_3$ and brine, dried ($Na_2SO_4$) and concentrated to a residue which was purified by column chromatography on silica gel with a gradient elution of 10:1 to 1:1 hexanes/ethyl acetate to provide the title compound. MS (DCI/$NH_3$) m/e 258 $(M+H)^+$ and 275 $(M+NH_4)^+$.

Example 14D (R)-8-chloro-3-[4-[3-(2-methoxyphenyl)-1-pyrrolidinyl]butyl]pyrazino[2',3':4,5]thieno[3,2-d]pyrimidine-2,4(1H,3H)-dione, Dihydrochloride The title compound was prepared from Examples 14C and 2B according to the procedure in Example 1I. mp 178–186°

C.; $[\alpha]_D^{23}$=+6.40° (c 0.30, MeOH); $^1$H NMR (CD$_3$OD) δ 1.85–1.93 (m, 4H), 2.20–2.42 (m, 2H), 3.16–3.43 (m, 4H), 3.59–3.63 (m, 1H), 3.76–3.97 (m, 5H), 4.13–4.15 (m, 2H), 6.97 (t, 1H), 7.02 (d, 1H), 7.25–7.32 (m, 2H), 8.83 (s, 1H); MS (DCI/NH$_3$) m/e 486 (M+H)$^+$; Anal. calcd for C$_{23}$H$_{24}$N$_5$O$_3$SCl.1.7 HCl.0.33(C$_2$H$_5$)$_2$O: C, 50.98; H, 5.07; N, 12.28. Found: C, 50.86; H, 5.00; N, 12.25.

EXAMPLE 15

(R)-8-Methoxy-3-[4-[3-(2-methoxyphenyl)-1-pyrrolidinyl]butyl]pyrazino-[2',3':4,5]thieno[3,2-d]pyrimidine-2,4(1H,3H)-dione, Dihydrochloride

Example 15A

Ethyl 7-amino-2-methoxy-thieno[2,3-b]pyrazine-6-carboxylate

A solution of Example 14C (0.700 g, 2.72 mmol) in methanol (75 mL) was treated with solid sodium methoxide (1.47 g, 27.2 mmol), refluxed for 12 hours, cooled and partitioned between saturated aqueous NH$_4$Cl and chloroform. The aqueous phase was extracted with chloroform, and the combined organic extracts were washed with water and brine, dried (Na$_2$SO$_4$) and concentrated to provide the title compound. MS (DCI/NH$_3$) m/e 240 (M+H)$^+$, and 257 (M+NH$_4$)$^+$.

Example 15B (R)-8-methoxy-3-[4-[3-(2-methoxyphenyl)-1-pyrrolidinyl]butyl]pyrazino-[2',3':4.5]thieno[3,2-d]pyrimidine-2,4(1H,3H)-dione, Dihydrochloride The title compound was prepared from Examples 15C and 2B according to the procedure in Example 1I. mp 170–182° C.; $[\alpha]_D^{23}$=+2.20 (c 0.27, MeOH); $^1$H NMR (CD$_3$OD) δ 0.85–1.96 (m, 4H), 2.21–2.44 (m, 2H), 3.17–3.48 (m, 4H), 3.60–3.63 (m, 1H), 3.73–3.95 (m, 5H), 4.12–4.18 (m, 5H), 6.95 (tt, 1H), 7.03 (d, 1H), 7.22–7.32 (m, 2H), 8.40 (s, 1H); MS (APCI(+)) m/e 482 (M+H)$^+$; Anal. calcd. for C$_{24}$H$_{26}$N$_5$O$_4$S.1.8HCl: C, 52.78; H, 5.13; N, 12.82. Found: C, 52.79; H, 5.42; N, 12.76.

EXAMPLE 16

(R)-8-phenyl-3-[4-[3-(2-methoxyphenyl)-1-pyrrolidinyl]butyl]pyrazino[2',3':4.5]thieno[3,2-d]pyrimidine-2,4(1H,3H)-dione, Dihydrochloride

Example 16A

2-Chloro-3-cyano-5-phenylpyrazine and 2-chloro-3-cyano-6-phenylpyrazine

A mixture of 5- and 6-phenyl regioisomers of 2-hydroxy-3-carboxamidopyrazines (7.2 g, 33.5 mmol) prepared by the method of R. G. Jones, J. Am. Chem. Soc. 71:78 (1949), was treated with phosphorous oxychloride (56 ml, 586 mmol) and triethylamine (9.3 mL, 67 mmol), heated to reflux for 2 hours and concentrated to provide a black oil which was extracted with ether. The extracts were washed with 10% aqueous Na$_2$CO$_3$, and the combined aqueous washings were back-extracted with ether. The combined organic extracts were decolorized with activated carbon, filtered through Celite® and evaporated to provide a white solid as a 60:40 mixture of the 5- and 6-phenyl isomers. mp (mixture) 121–125° C.; MS (DCI/NH$_3$) m/e 215 (M+H)$^+$.

Example 16B

Methyl 7-amino-3-phenylthieno[2 3-b]pyrazine-6-carboxylate

A solution of Example 16A (1.20 g, 5.58 mmol) in anhydrous DMF (5 ml) was treated sequentially with methyl thioglycolate (0.65 g, 6.14 mmol) and sodium methoxide (0.60 g, 11.2 mmol), stirred at 25° C. for 1 hour and diluted with water. The product was collected by filtration and purified by column chromatography on silica gel with methylene chloride to provide (first eluting isomer) of the title compound. MS (DCI/NH$_3$) m/e 286 (M+H)$^+$.

Example 16C (R)-8-phenyl-3-[4-[3-(2-methoxyphenyl)-1-pyrrolidinyl]butyl]pyrazino[2',3':4,5]thieno[3,2-d]pyrimidine-2,4(1H,3H)-dione, Dihydrochloride The title compound was prepared from Examples 16B and 2B according to the procedure in Example 1I. mp 161–165° C.; $[\alpha]_D^{23}$=−10.62 (c 0.04, MeOH); $^1$H NMR (300 MHz, CD$_3$OD) δ 1.86–1.92 (m, 4H), 2.23–2.44 (m, 2H), 3.18–3.38 (m, 4H), 3.61–3.73 (m, 1H), 3.76–3.92 (m, 5H), 4.11–4.18 (m, 2H), 6.96 (t,1H), 7.01 (d, 1H), 7.25 (q, 2H), 7.56 (m, 3H), 8.25 (m, 2H), 9.30 (s, 1H); MS (DCI/NH$_3$) m/e 528 (M+H)$^+$; Anal. calc'd for C$_{29}$H$_{29}$N$_5$O$_3$S.2HCl: C, 57.99; H, 5.20; N, 11.66. Found: C, 57.82; H, 5.33; N, 11.54.

EXAMPLE 17

(R)-2-[4-[3-(2-methoxyphenyl)-1-pyrrolidinyl]butyl]-1,2-benzoisothiazol-3(2H)-one. 1,-dioxide, Monohydrochloride

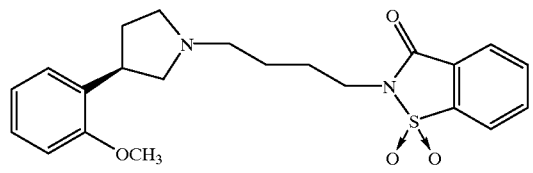

Example 17A 2-(4-bromobutyl)-1,2-benzoisothiazol-3(2H)-one, 1.1-dioxide

A slurry of NaH (60% in mineral oil, 480 mg, 20 mmol) in DMF (20 mL) was treated with 1,2-benzoisothiazol-3(2H)-one, 1,1-dioxide (3.66 mg, 20 mmol), stirred for 15 minutes, treated with 1,4-dibromobutane (21.9 mg, 100 mmol), stirred for 18 hours, treated with water and extracted with diethyl ether. The extracts were dried (Na$_2$SO$_4$) and concentrated, and the residue was azeotroped with toluene and purified on silica gel with 35:65 ethyl acetate/hexanes to provide the title compound. MS (DCI/NH$_3$) m/e 319 (M+H)$^+$.

Example 17B (R)-2-[4-[3-(2-methoxyphenyl)-1-pyrrolidinyl]butyl]-1,2-benzoisothiazol-3(2H)-one, 1,1-dioxide Monohydrochloride The title compound was prepared from Examples 17A and 1E according to the procedure in Example 1F and purified according to the procedure in Example 1I. mp 86–88° C.; $[\alpha]_D^{23}$=−1.8° (c 0.005, MeOH); $^1$H NMR (300 MHz, CD$_3$OD) δ 1.82 (bs, 4H), 2.18 (m, 2H), 3.38 (m, 3H), 3.62 (m, 2H), 3.78 (m, 2H), 3.90 (s, 3H), 3.95 (m, 1H), 4.15 (t, 2H), 6.95 (t, 1H), 7.15 (d, 1H), 7.25 (m, 2H), 7.9 (m, 2H), 8.10 (m, 2H); MS (DCI/NH$_3$) m/e 415 (M+H)$^+$; Anal. calc'd. for C$_{23}$H$_{26}$N$_2$O$_3$.HCl.1.0H$_2$O: C, 56.34; H, 6.23; N, 5.97. Found: C, 56.35; H, 6.12; N, 5.76.

EXAMPLE 18

(R)-4-[4-[3-(2-methoxyphenyl)-1-pyrrolidinyl]
butyl]-2H-1,4-benzoxazin-3 (4H)-one,
Monohydrochloride

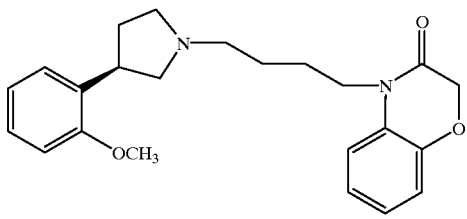

Example 18A 4-(4-bromobutyl)-2H-1 4-benzoxazin-3(4H)-one

The title compound was prepared from 2H-1,4-benzoxazin-3(4H)-one according to the procedure in Example 1 7A. MS (DCI/NH$_3$) m/e 285 (M+H)$^+$.

Example 18B (R)-4-[4-[3-(2-methoxyphenyl)-1-pyrrolidinyl]
butyl]-2H-1,4-benzoxazin-3(4H)-one,
Monohydrochloride The title compound was prepared from Examples 18A and 1E according to the procedure in Example 1F and purified according to the procedure in Example 1I. mp 66–70° C.; $[\alpha]_D^{23}$=–0.5° (c 0.002, MeOH); $^1$H NMR (300 MHz, MeOH) δ 1.78 (bs, 5H), 2.20–2.45 (m, 3H), 3.25 (m, 2H), 3.58 (bd, 2H), 3.65–3.82 (m, 3H), 3.85 (s, 3H), 4.05 (t, J=6 Hz, 2H), 7.00 (m, 5H), 7.25 (m, 3H); MS (DCI/NH$_3$) m/e 381 (M+H)$^+$; Anal. calcd. for C$_{24}$H$_{28}$N$_2$O$_3$·1.0HCl0.5 H$_2$O·0.3C$_2$H$_5$OH: C, 64.46; H, 7.29; N, 6.37. Found: C, 64.48; H, 7.10; N, 6.01.

EXAMPLE 19

(R)-3,4-dihydro-1-[4-[3-(2-methoxyphenyl)-1-
pyrrolidinyl]butyl]-2(1H)-quinolinone
Monohydrochloride

Example 19A 1-(4-bromobutyl)-3,4-dihydro-2(1H)-quinolinone

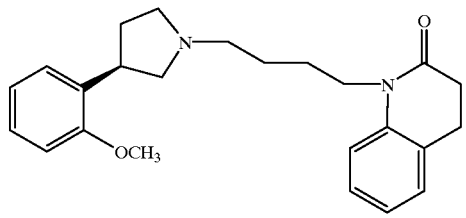

The title compound was prepared from 3,4-Dihydro-2 (1H)-quinolinone according to the procedure in Example 1 7A. MS (DCI/NH$_3$) m/e 283 (M+H)$^+$.

Example 19B (R)-3,4-dihydro-1-[4-[3-(2-methoxyphenyl)-1-
pyrrolidinyl]butyl]-2(1H)-quinolinone
Monohydrochloride The title compound was prepared from Examples 19A and 1E according to the procedure in Example 1F and purified according to the procedure in Example 1I. mp >200° C.; $[\alpha]_D^{23}$=+0.4° (c 0.005, MeOH); $^1$H NMR (300 MHz, MeOH) δ 1.78 (bs, 5H), 2.28 (m, 1H), 2.41 (m, 1H), 2.62, (t, 2H), 2.90 (t, 2H), 3.53–3.81 (m, 5H), 3.86 (s, 3H), 4.05 (t, 2H) (6.98 (t, 1H), 7.02 (d, 2H), 7.22 (m, 5H); MS (DCI/NH$_3$) m/e 379 (M+H)$^+$; Anal. calcd. for C$_{23}$H$_{26}$N$_2$O$_3$·HCl 0.5H$_2$O·0.3C$_2$H$_5$OH: C, 67.47; H, 7.78; N, 6.4. Found: C, 67.44; H, 7.53; N, 6.47.

EXAMPLE 20

(R)-3-[2-[3-(3-methoxyphenyl)-1-pyrrolidinyl]ethyl]
pyrido[2',3':4,5]thieno[3,2-d]pyrimidine-2,4(1H,3H)-
dione, Dihydrochloride The title compound was prepared from Examples 3F and 4A according to the procedure in Example 11. mp 217–220° C.; $[\alpha]_D^{23}$=+11.7° (c 0.002, MeOH); $^1$H NMR (CD$_3$OD) δ 2.30 (m, 1H), 2.51 (m, 1H), 3.38 (m, 1H), 3.56 (m, 2H), 3.69 (m, 2H), 3.80 (s, 3H), 4.01 (m, 1H), 4.18 (q, 1H), 4.48 (t, 2H), 6.89 (m, 3H), 7.25 (t, 1H), 7.61 (q, 1H), 8.47 (d, 1H), 8.81 (d, 1H); MS (DCI/NH$_3$) m/e 423 (M+H)$^+$; Anal. calcd for C$_{22}$H$_{22}$N$_4$O$_3$S·2.0HCl: C, 53.34; H, 4.88; N, 11.31. Found: C, 52.62; H, 4.85; N, 11.02.

EXAMPLE 21

(R)-3-[3-[3-(3-methoxyphenyl)-1-pyrrolidinyl]
propyl]pyrido[2',3':4,5]thieno[3 .2-d]pyrimidine-2,4
(1H,3H)-dione, Dihydrochloride

Example 21A (R)-3-(3-Methoxyphenyl)-1-
pyrrolidinepropanenitrile

The title compound was prepared from Example 3D according to the procedure in Example 5A. MS (DCI/NH$_3$) m/e 231 (M+H)$^+$.

Example 21B (R)-3-(3-Methoxyphenyl)-1-
pyrrolidinylpropanamine

The title compound was prepared from Example 21 A according to the procedure in Example 1G. MS (DCI/NH$_3$) m/e 235 (M+H)$^+$.

Example 21C (R)-3-[3-[3-(3-methoxyphenyl)-1-pyrrolidinyl]
propyl]pyrido[2',3':4,5]thieno[3,2-d]pyrimidine-2,4
(1H,3 H)-dione, Dihydrochloride The title compound was prepared from Examples 21B and 4A according to the procedure in Example 11. mp 259–261° C.; $[\alpha]_D^{23}$=+6.2° (c 0.002, MeOH); $^1$H NMR (CD$_3$OD) δ 2.20 (m, 3H), 2.51 (m, 1H), 3.20 (m, 1H), 3.40 (m, 3H), 3.50–3.76 (m, 2H), 3.79 (s, 1.5H), 3.80 (s, 1.5H), 3.99 (q, 1H), 4.22 (t, 2H), 6.89 (m, 3H), 7.25 (t, 1H), 7.61 (q, 1H), 8.47 (d, 1H), 8.81 (d, 1H); MS (DCI/NH$_3$) m/e 437 (M+H)$^+$; Anal. calcd for C$_{23}$H$_{24}$N$_4$O$_3$S·2.0 HCl: C, 54.23, H, 5.14, N, 11.00, Found: C, 53.68, H, 5.07, N, 10.78.

EXAMPLE 22

(R)-3-[4-[3-(3-methoxyphenyl)-1-pyrrolidinyl]butyl]
pyrido[2',3 ':4,5]thieno[3,2-d]pyrimidine-2,4(1H,
3H)-dione, Dihydrochloride

Example 22A (R)-3-(3-Methoxyphenyl)-1-pyrrolidinebutanenitrile

The title compound was prepared from Example 3D according to the procedure in Example 2A. MS (DCI/NH$_3$) m/e 245 (M+H)$^+$.

Example 22B (R)-3-(3-Methoxyphenyl)-1-pyrrolidinebutanamine

The title compound was prepared from Example 22A according to the procedure in Example 1G. MS (DCI/NH$_3$) m/e 219 (M+H)$^+$.

Example 22C (R)-3-[4-[3-(3-methoxyphenyl)-1-pyrrolidinyl]butyl] pyrido[2',3':4,5]thieno[3,2-d]pyrimidine-2,4(1H,3H)-dione, Dihydrochloride The title compound was prepared from Examples 22B and 4A according to the procedure in Example 11. mp >250° C.; $[\alpha]_D^{23}$=+22.7° (c 0.002, MeOH); $^1$H NMR (CD$_3$OD) δ 1.82 (bs, 4H), 2.20 (m, 3H), 2.51 (m, 1H), 3.20 (m, 1H), 3.40 (m, 3H), 3.50–3.76 (m, 2H), 3.79 (s, 1.5H), 3.80 (s, 1.5H), 3.99 (q, 1H), 4.22 (t, 2H), 6.89 (m, 3H), 7.25 (t, 1H), 7.61 (q, 1H), 8.47 (d, 1H), 8.81 (d, 1H); MS (DCI/NH$_3$) m/e 451 (M+H)$^+$; Anal. calcd for C$_{24}$H$_{26}$N$_4$O$_3$S.2.0HCl.0.5 MeOH: C, 55.07; H, 5.39; N, 10.70. Found: C, 54.60; H, 5.52; N, 10.39.

EXAMPLE 23

(R)-3-[2-[3-(3-methoxyphenyl)-1-pyrrolidinyl]ethyl] pyrido[3',2':4,5]thieno[3,2-d]pyrimidine-2,4(1H,3H)-dione, Dihydrochloride The title compound was prepared from Examples 1G and 8A according to the procedure in Example 11. mp >250° C.; $[\alpha]_D^{23}$=+8.8° (c 0.002, MeOH); $^1$H NMR (CD$_3$OD) δ 2.28 (m, 1H), 2.50 (m, 1H), 3.38 (m, 1H), 3.58 (m, 1H), 3.69 (m, 3H), 3.81 (s, 3H), 4.00 (m, 1H), 4.18 (q, 1H), 4.22 (t, 2H), 6.90 (m, 3H), 7.25 (t, 1H), 7.60 (q, 1H), 8.59 (d, 1H), 8.79 (d, 1H); MS (DCI/NH$_3$) m/e 423 (M+H)$^+$; Anal. calcd for C$_{22}$H$_{22}$N$_4$O$_3$S.2.0HCl: C, 53.34 ; H, 4.88; N, 1 1.3 1. Found: C, 50.84; 4.98; N, 10.30.

EXAMPLE 24

(R)-3-[4-[3-(3-methoxyphenyl)-1-pyrrolidinyl]butyl] pyrido[3',2':4,5]thieno[3,2-d]pyrimidine-2,4(1H,3H)-dione, Dihydrochloride The title compound was prepared from Examples 22B and 8A according to the procedure in Example 11. mp 135–138° C.; $[\alpha]_D^{23}$=+13.5° (c 0.002, MeOH); $^1$H NMR (CD$_3$OD) δ 1.82 (bs, 4H), 2.20 (m, 1H), 2.50 (m, 1H), 3.38 (m, 3H), 3.62 (m, 2H), 3.76 (m, 2H), 3.79 (s, 3H), 3.98 (q, 1H), 4.15 (t, 2H), 6.90 (m, 3H), 7.28 (m, 1H), 7.60 (q, 1H), 8.45 (d, 0.5H), 8.46 (d, 0.5H), 8.81 (d, 0.5H), 8.82 (d, 0.5H). MS (DCI/NH$_3$) m/e 451 (M+H)$^+$; Anal. calcd for C$_{24}$H$_{26}$N$_4$O$_3$S.2.0HCl.0.4MeOH: C, 54.65; H; 5.56, N, 10.45. Found: C, 54.44; H, 5.67; N, 10.37.

EXAMPLE 25

(S)-3-[2-[3-(2-methoxyphenyl)-1-pyrrolidinyl] ethyl]-[1]benzothieno[3,2-d]pyrimidine-2,4(1H,3H)-dione Monohydrochloride

Example 25A (S)-3-Acetyl-4-(phenylmethyl)-2-oxazolidinone

The title compound was prepared from (S)-(–)-4-benzyl oxazolidinone according to the reference in Example 1A. MS (DCI/NH$_3$) m/e 220 (M+H)$^+$.

Example 25B (S,S)-3-[3-(2-Methoxyphenyl)-4-nitro-1-oxobutyl]-4-(phenylmethyl)-2-oxazolidinone The title compound was prepared from Example 25A according to the procedure in Example 1B. MS (DCI/NH$_3$) m/e 416 (M+H)$^+$.

Example 25C (S)-2-methoxy-β-(nitromethyl)benzenepropanoic Acid

The title compound was prepared from Example 25B according to the procedure in Example 1C. MS (DCI/NH$_3$) m/e 257 (M+H)$^+$.

Example 25D (S)-4-(2-Methoxyphenyl)-2-pyrrolidinone

The title compound was prepared from Example 25C according to the procedure in Example 1D. MS (DCI/NH$_3$) m/e 192 (M+H)$^+$.

Example 25E (S)-3-(2-methoxyphenyl)pyrrolidine

The title compound was prepared from Example 25D according to the procedure in Example 1E. MS (DCI/NH/) m/e 178 (M+H)$^+$.

Example 25F (S)-3-(3-Methoxyphenyl)-1-pyrrolidineacetonitrile

The title compound was prepared from Example 25E according to the procedure in Example 1F. MS (DCI/NH$_3$) m/e 217 (M+H)$^+$.

Example 25G (S)-3-(2-Methoxyphenyl)-1-pyrrolidineethanamine

The title compound was prepared from Example 25F according to the procedure in Example 1G. MS (DCI/NH$_3$) m/e 221 (M+H)$^+$.

Example 25H (S)-3-[2-[3-(2-methoxyphenyl)-1-pyrrolidinyl] ethyl]-[1]benzothieno[3,2-d]pyrimidine-2,4(1H,3H)-dione, Monohydrochloride The title compound was prepared from Examples 25G and 1H according to the procedure in Example 1I. mp >250° C.; $[\alpha]_D^{23}$=+1.58° (c 0.002, MeOH); $^1$H NMR (CD$_3$OD) δ 2.19–2.55 (m, 2H), 3.30 (m, 1H), 3.55 (m, 1H), 3.67 (t, 3H), 3.78 (m, 1H), 3.90 (s, 3H), 4.00 (m, 1H), 4.16 (q, 1H), 4.48 (t, 2H), 6.98 (m, 2H), 7.28 (m, 2H), 7.60 (m, 2H), 8.01 (d, 1H), 8.21 (d, 1H); MS (DCI/NH$_3$) m/e 422 (M+H)$^+$; Anal. calcd for C$_{23}$H$_{23}$N$_3$O$_3$S.1.7HCl: C, 57.14; H, 5.15; N, 8.69. Found: C, 57.02; H, 5.29; N. 8.43.

EXAMPLE 26

(S)-3-[2-[3-(3-methoxyphenyl)-1-pyrrolidinyl] ethyl]-[1]benzothieno[3,2-d]pyrimidine-2,4(1H,3H)-dione, Monohydrochloride

Example 26A (S,S)-3-[3-(3-Methoxyphenyl)-4-nitro-1-oxobutyl]-4-(phenylmethyl)-2-oxazolidinone The title compound was prepared from Example 25A according to the procedure in Example 3A. MS (DCI/NH$_3$) m/e 416 (M+H)$^+$.

Example 26B (S)-3-methoxy-β-(nitromethyl)benzenepropanoic Acid

The title compound was prepared from Example 26A according to the procedure in Example 1C. MS (DCI/NH$_3$) m/e 257 (M+H)$^+$.

Example 26C

(S)-4-(3-Methoxyphenyl)-2-pyrrolidinone

The title compound was prepared from Example 26B according to the procedure in Example 1D. MS (DCI/NH$_3$) m/e 192 (M+H)$^+$.

Example 26D

(S)-3-(3-methoxyphenyl)pyrrolidine

The title compound was prepared from Example 26C according to the procedure in Example 1E. MS (DCI/NH$_3$) m/e 178 (M+H)$^+$.

Example 26E

(S)-3-(3-Methoxyphenyl)-1-pyrrolidineacetonitrile

The title compound was prepared from Example 26D according to the procedure in Example 1F. MS (DCI/NH$_3$) m/e 217 (M+H)$^+$.

Example 26F

(S)-3-(3-Methoxyphenyl)-1-pyrrolidineethanamine

The title compound was prepared from Example 26E according to the procedure in Example 1G. MS (DCI/NH$_3$) m/e 221 (M+H)$^+$.

Example 26G

(S)-3-[2-[3-(3-methoxyphenyl)-1-pyrrolidinyl]ethyl]-[1]benzothieno[3,2-d]pyrimidine-2,4(1H,3H)-dione, Monohydrochloride The title compound was prepared from Examples 26F and 1H according to the procedure in Example 1I. mp >250° C.; [α]$_D^{23}$=−1.58° (c 0.002, MeOH); $^1$H NMR (300 MHz, CD$_3$OD) δ 2.19–2.55 (m, 2H), 3.30 (m, 1H), 3.55 (m, 1H), 3.67 (t, 3H), 3.78 (m, 1H), 3.90 (s, 3H), 4.00 (m, 1H), 4.16 (q, 1H), 4.48 (t, 2H), 6.98 (m, 2H), 7.28 (m, 2H), 7.60 (m, 2H), 8.01 (d, 1H), 8.21 (d, 1H); MS (DCI/NH$_3$) m/e 422 (M+H)$^+$; Anal. calcd. for C$_{23}$H$_{23}$N$_3$O$_3$S.1.7HCl: C, 57.14; H, 5.15; N, 8.69. Found: C, 57.02; H, 5.29; N, 8.43.

EXAMPLE 27

(S)-3-[2-[3-(2-methoxyphenyl)-1-pyrrolidinyl]ethyl]pyrido[2',3':4,5]thieno[3,2-d]pyrimidine-2,4(1H,3H)-dione, Dihydrochloride The title compound was prepared from Examples 25G and 4A according to the procedure in Example 1I. mp 206–209° C.; [α]$_D^{23}$=+3.4° (c 0.001, MeOH); $^1$H NMR (CD$_3$OD) δ 2.19–2.55 (m, 2H), 3.30 (m, 1H), 3.55 (m, 1H), 3.67 (t, 2H), 3.78 (m, 1H), 3.86 (s, 1.5H), 3.91 (s, 1.5H), 4.00 (m, 1H), 4.16 (q, 1H), 4.48 (t, 2H), 6.95 (m, 1H), 7.02 (d, 1H), 7.25 (q, 2H), 7.61 (q, 1H), 8.50 (d, 1H), 8.81 (d, 1H); MS (DCI/NH$_3$) m/e 423 (M+H)$^+$; Anal. calcd for C$_{22}$H$_{22}$N$_4$O$_3$S: C, 53.34; H, 4.88; N, 11.31. Found: C, 53.77; H, 4.85; N, 11.13.

EXAMPLE 28

(S)-3-[3-[3-(2-methoxyphenyl)-1-pyrrolidinyl]propyl]pyrido[2',3':4,5]thieno[3,2-d]pyrimidine-2,4(1H,3H)-dione, Dihydrochloride

Example 28A

(S)-3-(3-Methoxyphenyl)-1-pyrrolidinepropanenitrile

The title compound was prepared from Example 25E according to the procedure in Example 5A. MS (DCI/NH$_3$) m/e 231 (M+H)$^+$.

Example 28B

(S)-3-(3-Methoxyphenyl)-1-pyrrolidinepropanamine

The title compound was prepared from Example 28A according to the procedure in Example 5B. MS (DCI/NH$_3$) m/e 235 (M+H)$^+$.

Example 28C

(S)-3-[3-[3-(2-methoxyphenyl)-1-pyrrolidinyl]propyl]pyrido[2',3':4,5]thieno[3,2-d]pyrimidine-2,4(1H,3 H)-dione, Dihydrochloride The title compound was prepared from Examples 28C and 4A according to the procedure in Example 1I. mp 200° C. (dec); [α]$_D^{23}$=+3.2° (c 0.003, MeOH); $^1$H NMR (CD$_3$OD) δ 2.21 (m, 2H), 2.30–2.57 (m, 2H), 3.39 (t, 3H), 3.58–3.82 (m, 3H), 3.84 (s, 1.5H), 3.91 (s, 1.5H), 3.99 (m, 1H), 4.21 (m, 2H), 6.99 (m, 1H), 7.02 (d, 1H), 7.23 (m, 2H), 7.60 (q, 1H), 8.50 (d, 1H), 8.81 (d, 1H); MS (DCI/NH$_3$) m/e 437 (M+H)$^+$; Anal. calcd for C$_{23}$H$_{24}$N$_4$O$_3$S.2.2HCl.1.0C$_4$H$_8$O$_2$: C, 53.62; H, 5.70; N, 9.26. Found: C, 53.58; H, 5.57; N, 9.29.

EXAMPLE 29

(S)-3-[4-[3-(2-methoxyphenyl)-1-pyrrolidinyl]butyl]pyrido[2',3':4,5]thieno[3,2-d]pyrimidine-2,4(1H,3H)-dione, Dihydrochloride

Example 29A

(S)-3-(2-Methoxyphenyl)-1-pyrrolidinebutanenitrile

The title compound was prepared from Example 25E according to the procedure in Example 2A. MS (DCI/NH$_3$) m/e 245 (M+H)$^+$.

Example 29B

(S)-3-(2-Methoxyphenyl)-1-pyrrolidinebutanamine

The title compound was prepared from Example 29A according to the procedure in Example 2B. MS (DCI/NH$_3$) m/e 249 (M+H)$^+$.

Example 29C

(S)-3-[4-[3-(2-methoxyphenyl)-1-pyrrolidinyl]butyl]pyrido[2',3':4,5]thieno[3,2-d]pyrimidine-2,4(1H,3H)-dione, Dihydrochloride The title compound was prepared from Examples 29B and 4A according to the procedure in Example 1I. mp 125–130° C.; [α]$_D^{23}$=−2,3° (c 0.007, MeOH); $^1$H NMR (CD$_3$OD) δ 1.75 (bs, 2H), 1.90 (bs, 2H), 2.37 (bd, 2H), 3.10–3.50 (m, 5H), 3.61 (bs, 1H), 3.79 (m, 1H), 3.85 (s, 1.5H), 3.87 (s, 1.5H), 3.99 (s, 2H), 6.98 (t, 1H), 7.00 (d, 1H), 7.24 (m, 2H), 7.90 (m, 1H), 8.90 (d, 2H); MS (DCI/NH$_3$) m/e 451 (M+H)$^+$; Anal. calcd for C$_{24}$H$_{26}$N$_4$O$_3$S.2.0HCl 1.30H$_2$O: C, 52.71; H, 5.64; N, 10.24. Found: C, 52.78; H, 5.77; N, 9.85.

We claim:
1. A compound of formula (I)

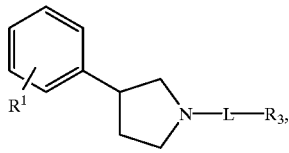

(I)

wherein

R₁ represents 1 or more optional substituents independently selected from the group consisting of
$C_{1-8}$ alkyl;
$C_{2-8}$ alkenyl;
$C_{2-8}$ alkynyl;
alkoxyalkyl, wherein the alkyl and alkylene groups are independently $C_{1-8}$;
$C_{1-8}$ alkoxy;
$C_{1-8}$ alkoxycarbonyl;
hydroxy;
$C_{1-8}$ hydroxyalkyl;
carboxy;
O-protected carboxy;
$C_{1-8}$ carboxyalkyl;
O-protected $C_{1-8}$ carboxyalkyl;
halo;
amino;
N-protected amino;
$C_{1-8}$ aminoalkyl; and
$C_{1-8}$ N-protected aminoalkyl;
L is $C_{2-8}$ alkylene; and
R₃ is selected from the group consisting of

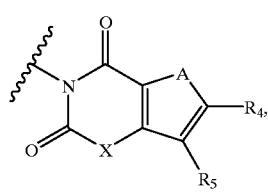

(1)

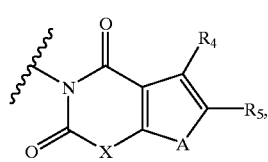

(3)

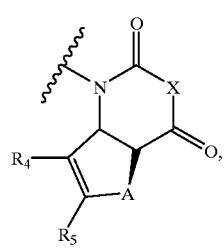

(5)

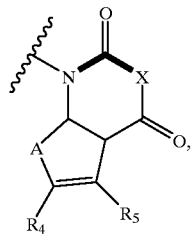

(6)

wherein, for (1), (3), (5) and (6), R₄ and R₅ together form a ring which is fused to its adjacent ring and is selected from the group consisting of
(a) a five-membered carbocyclic ring and
(b) a five-membered ring having four carbon atoms and one heteroatom selected from the group consisting of
nitrogen,
oxygen, and
sulfur;
(c) a five-membered ring having three carbon atoms and two heteroatoms independently selected from the group consisting of
nitrogen,
oxygen, and
sulfur;
(d) a six-membered carbocyclic ring;
(e) a six-membered ring having five carbon atoms and one heteroatom selected from the group consisting of
nitrogen,
oxygen, and
sulfur;
(f) a six-membered ring having four carbon atoms and two heteroatoms selected from the group consisting of
nitrogen,
oxygen, and
sulfur;
(g) a six-membered ring having three carbon atoms and three heteroatoms selected from the group consisting of
nitrogen,
oxygen, and
sulfur;
wherein the five-membered rings formed by R₄ and R₅ together with the ring to which they are fused have 1 or 2 double bonds, and wherein the six-membered rings formed by R₄ and R₅ together with the ring to which they are fused have 1, 2 or 3 double bonds, and wherein the rings formed by R₄ and R₅ together are optionally substituted with one or two substituents independently selected from the group consisting of
$C_{1-8}$ alkyl;
$C_{1-8}$ alkoxy;
cyano;
nitro;
carboxy;
$C_{1-8}$ alkoxycarbonyl;
halo;
$C_{3-8}$ cycloalkyl;
aryl; and
heterocycle,
A is selected from the group consisting of
—O—;

—S(O)$_t$—, wherein t is zero to two, and
—NR$_6$—, and

X is —NR$_6$—; and or a pharmaceutically acceptable salt, ester or prodrug thereof.

2. The compound according to claim 1 wherein R$_1$ is selected from the group consisting of a 2-C$_{1-8}$ alkoxy and a 3-C$_{1-8}$ alkoxy; R$_3$ is selected from the group consisting of structures (1) and wherein the ring formed by R$_4$ and R$_5$ is selected from the group consisting of (d), (e) and (f).

3. The compound according to claim 2 wherein R$_3$ is selected from the group consisting of substituted or unsubstituted benzothieno[3,2-d]pyrimidine-2,4(1H,3H)-dione, pyrido[2',3':4,5]thieno[3,2-d]pyrimidine-2,4(1H,3H)-dione, pyrido[3',2':4,5]thieno[3,2-d]pyrimidine-2,4(1H,3H)-dione, and pyrazino[2',3':4,5]thieno[3,2-d]pyrimidine-2,4(1H,3H)-dione.

4. A compound selected from the group consisting of:
(R)-3-[2-[3-(2-Methoxyphenyl)-1-pyrrolidinyl]ethyl]-[1]benzothieno[3,2-d]pyrimidine-2,4(1H,3H)-dione;
(R)-3-[4-[3-(2-Methoxyphenyl)-1-pyrrolidinyl]butyl]-[1]benzothieno[3,2-d]pyrimidine-2,4(1H,3H)-dione;
(R)-3-[2-[3-(3-Methoxyphenyl)-1-pyrrolidinyl]ethyl]-[1]benzothieno[3,2-d]pyrimidine-2,4(1H,3H)-dione;
(R)-3-[2-[3-(2-Methoxyphenyl)-1-pyrrolidinyl]ethyl]pyrido[2',3':4,5]thieno[3,2-d]pyrimidine-2,4(1H,3H)-dione;
(R)-3-[3-[3-(2-Methoxyphenyl)-1-pyrrolidinyl]propyl]pyrido[2',3':4,5]thieno[3,2-d]pyrimidine-2,4(1H,3H)-dione;
(R)-3-[4-[3-(2-Methoxyphenyl)-1-pyrrolidinyl]butyl]pyrido[2',3':4,5]thieno[3,2-d]pyrimidine-2,4(1H,3H)-dione;
(R)-3-[5-[3-(2-Methoxyphenyl)-1-pyrrolidinyl]pentyl]pyrido[2',3 ':4,5]thieno[3,2-d]pyrimidine-2,4(1H,3H)-dione;
(R)-3-[4-[3-(2-Methoxyphenyl)-1-pyrrolidinyl]butyl]pyrido[3',2':4,5]thieno[3,2-d]pyrimidine-2,4(1H,3H)-dione;
(R)-3-[5-[3-(2-methoxyphenyl)-1-pyrrolidinyl]pentyl]pyrido[3 ',2':4,5]thieno[3,2-d]pyrimidine-2,4(1H,3H)-dione;
(R)-8-chloro-3-[4-[3-(2-methoxyphenyl)-1-pyrrolidinyl]butyl]pyrido[2',3':4,5]thieno[3,2-d]pyrimidine-2,4(1H,3H)-dione;
(R)-8-methoxy-3-[4-[3-(2-methoxyphenyl)-1-pyrrolidinyl]butyl]pyrido[2',3 ':4,5]thieno[3,2-d]pyrimidine-2,4(1H,3H)-dione;
(R)-3-[4-[3-(2-Methoxyphenyl)-1-pyrrolidinyl]butyl]pyrazino[2',3':4,5]thieno[3,2-d]pyrimidine-2,4(1H,3H)-dione;
(R)-8-Chloro-3-[4-[3-(2-methoxyphenyl)-1-pyrrolidinyl]butyl]pyrazino[2',3':4,5]thieno[3,2-d]pyrimidine-2,4(1H,3H)-dione;
(R)-8-Methoxy-3-[4-[3-(2-methoxyphenyl)-1-pyrrolidinyl]butyl]pyrazino[2',3 ':4,5]thieno[3,2-d]pyrimidine-2,4(1H,3H)-dione;
(R)-8-phenyl-3-[4-[3-(2-methoxyphenyl)-1-pyrrolidinyl]butyl]pyrazino[2',3':4,5]thieno[3,2-d]pyrimidine-2,4(1H,3H)-dione;
(R)-3-[2-[3-(3-methoxyphenyl)-1-pyrrolidinyl]ethyl]pyrido[2',3 ':4,5]thieno[3,2-d]pyrimidine-2,4(1H,3H)-dione;
(R)-3-[3-[3-(3-methoxyphenyl)-1-pyrrolidinyl]propyl]pyrido[2',3':4,5]thieno[3,2-d]pyrimidine-2,4(1H,3H)-dione;
(R)-3-[4-[3-(3-methoxyphenyl)-1-pyrrolidinyl]butyl]pyrido[2',3':4,5]thieno[3,2-d]pyrimidine-2,4(1H,3H)-dione;
(R)-3-[2-[3-(3-methoxyphenyl)-1-pyrrolidinyl]ethyl]pyrido[3',2':4,5]thieno[3,2-d]pyrimidine-2,4(1H,3H)-dione;
(R)-3-[4-[3-(3-methoxyphenyl)-1-pyrrolidinyl]butyl]pyrido[3',2':4,5]thieno[3,2-d]pyrimidine-2,4(1H,3H)-dione;
(S)-3-[2-[3-(2-methoxyphenyl)-1-pyrrolidinyl]ethyl]-[1]benzothieno[3,2-d]pyrimidine-2,4(1H,3H)-dione;
(S)-3-[2-[3-(3-methoxyphenyl)-1-pyrrolidinyl]ethyl]-[1]benzothieno[3,2-d]pyrimidine-2,4(1H,3H)-dione;
(S)-3-[2-[3-(2-methoxyphenyl)-1-pyrrolidinyl]ethyl]pyrido[2',3':4,5]thieno[3,2-d]pyrimidine-2,4(1H,3H)-dione;
(S)-3-[3-[3-(2-methoxyphenyl)-1-pyrrolidinyl]propyl]pyrido[2',3':4,5]thieno[3,2-d]pyrimidine-2,4(1H,3H)-dione; and
(S)-3-[4-[3-(2-methoxyphenyl)-1-pyrrolidinyl]butyl]pyrido[2',3':4,5]thieno[3,2-d]pyrimidine-2,4(1H,3H)-dione.

5. The compound according to claim 4 selected from the group consisting of:
(R)-3-[4-[3-(2-Methoxyphenyl)-1-pyrrolidinyl]butyl]pyrido[2',3':4,5]thieno[3,2-d]pyrimidine-2,4(1H,3H)-dione;
(R)-3-[4-[3-(2-Methoxyphenyl)-1-pyrrolidinyl]butyl]pyrido[3 ',2':4,5]thieno[3,2-d]pyrimidine-2,4(1H,3H)-dione;
(R)-8-methoxy-3-[4-[3-(2-methoxyphenyl)-1-pyrrolidinyl]butyl]pyrido[2',3':4,5]thieno[3,2-d]pyrimidine-2,4(1H,3H)-dione;
[(R)-2-[4-[3-(2-methoxyphenyl)-1-pyrrolidinyl]butyl]-1H-isoindole-1,3(2H)-dione;]
(R)-3-[4-[3-(2-Methoxyphenyl)-1-pyrrolidinyl]butyl]pyrazino[2',3':4,5]thieno[3,2-d]pyrimidine-2,4(1H,3H)-dione;
(R)-8-Chloro-3-[4-[3-(2-methoxyphenyl)-1-pyrrolidinyl]butyl]pyrazino[2',3':4,5]thieno[3,2-d]pyrimidine-2,4(1H,3H)-dione;
(R)-8-Methoxy-3-[4-[3-(2-methoxyphenyl)-1-pyrrolidinyl]butyl]pyrazino[2',3':4,5]thieno[3,2-d]pyrimidine-2,4(1H,3H)-dione; and
(R)-8-phenyl-3-[4-[3-(2-methoxyphenyl)-1-pyrrolidinyl]butyl]pyrazino[2',3':4,5]thieno[3,2-d]pyrimidine-2,4(1H,3H)-dione.

6. A compound of claim 1 of formula (I)

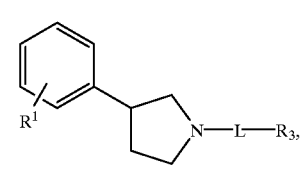

(I)

wherein

R$_1$ represents 1 or more optional substituents independently selected from the group consisting of
C$_{1-8}$ alkyl;
C$_{2-8}$ alkenyl;
C$_{2-8}$ alkynyl;
alkoxyalkyl, wherein the alkyl and alkylene groups are independently C$_{1-8}$;

$C_{1-8}$ alkoxy,
$C_{1-8}$ alkoxycarbonyl,
hydroxy;
$C_{1-8}$ hydroxyalkyl,
carboxy;
O-protected carboxy;
$C_{1-8}$ carboxyalkyl;
O-protected $C_{1-8}$ carboxyalkyl;
halo;
amino;
N-protected amino;
$C_{1-8}$ aminoalkyl; and
$C_{1-8}$ N-protected aminoalkyl;
L is $C_{2-8}$ alkylene; and
$R_3$ is

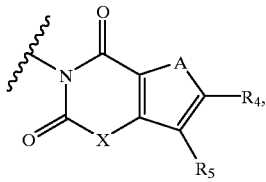

(1)

wherein $R_4$ and $R_5$ together form a ring which is fused to its adjacent ring and is selected from the group consisting of
  (a) a five-membered carbocyclic ring and
  (b) a five-membered ring having four carbon atoms and one heteroatom selected from the group consisting of
    nitrogen
    oxygen, and
    sulfur;
  (c) a five-membered ring having three carbon atoms and two heteroatoms independently selected from the group consisting of
    nitrogen,
    oxygen, and
    sulfur;
  (d) a six-membered carbocyclic ring;
  (e) a six-membered ring having five carbon atoms and one heteroatom selected from the group, consisting of
    nitrogen,
    oxygen, and
    sulfur;
  (f) a six-membered ring having four carbon atoms and two heteroatoms selected from the group consisting of
    nitrogen,
    oxygen, and
    sulfur;
  (g) a six-membered ring having three carbon atoms and three heteroatoms selected from the group consisting of
    nitrogen,
    oxygen, and
    sulfur;
wherein the five-membered rings formed by $R_4$ and $R_5$ together with the ring to which they are fused have 1 or 2 double bonds, and wherein the six-membered rings formed by $R_4$ and $R_5$ together with the ring to which they are fused have 1, 2 or 3 double bonds and wherein the rings formed by $R_4$ and $R_5$ together are optionally substituted with one or two substituents independently selected from the group consisting of
  $C_{1-8}$ alkyl;
  $C_{1-8}$ alkoxy;
  cyano,
  nitro;
  carboxy;
  $C_{1-8}$ alkoxycarbonyl;
  halo;
  $C_{3-8}$ cycloalkyl;
  aryl; and
  heterocycle,
A is selected from the group consisting of
  —O—;
  —S(O)$_t$—, wherein t is zero to two, and
  —NR$_6$—, and
X is —NR$_6$—,
or a pharmaceutically acceptable salt, ester or prodrug thereof.

7. A compound of claim 1 of formula (I)

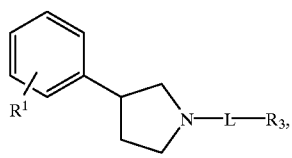

(I)

wherein
  $R_1$ represents 1 or more optional substituents independently selected from the group consisting of
    $C_{1-8}$ alkyl;
    $C_{2-8}$ alkenyl;
    $C_{2-8}$ alkynyl;
    alkoxyalkyl wherein the alkyl and alkylene groups are independently $C_{1-8}$;
    $C_{1-8}$ alkoxy;
    $C_{1-8}$ alkoxycarbonyl
    hydroxy;
    $C_{1-8}$ hydroxyalkyl;
    carboxy;
    O-protected carboxy;
    $C_{1-8}$ carboxyalkyl;
    O-protected $C_{1-8}$ carboxyalkyl;
    halo;
    amino;
    N-protected amino;
    $C_{1-8}$ aminoalkyl; and
    $C_{1-8}$ N-protected aminoalkyl;
  L is $C_{2-8}$ alkylene; and
  $R_3$ is

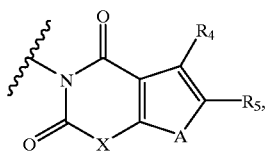

(3)

wherein $R_4$ and $R_5$ together form a ring which is fused to its adjacent ring and is selected from the group consisting of
  (a) a five-membered carbocyclic ring and
  (b) a five-membered ring having four carbon atoms and one heteroatom selected from the group consisting of
    nitrogen,
    oxygen, and
    sulfur;

(c) a five-membered ring having three carbon atoms and two heteroatoms independently selected from the group consisting of
nitrogen,
oxygen, and
sulfur;
(d) a six-membered carbocyclic ring,
(e) a six-membered ring having five carbon atoms and one heteroatom selected from the group consisting of
nitrogen,
oxygen, and
sulfur;
(f) a six-membered ring having four carbon atoms and two heteroatoms selected from the group consisting of
nitrogen,
oxygen, and
sulfur;
(g) a six-membered ring having three carbon atoms and three heteroatoms selected from the group consisting of
nitrogen,
oxygen, and
sulfur;
wherein the five-membered rings formed by $R_4$ and $R_5$ together with the ring to which they are fused have 1 or 2 double bonds, and wherein the six-membered rings formed by $R_4$ and $R_5$ together with the ring to which they are fused have 1, 2 or 3 double bonds, and wherein the rings formed by $R_4$ and $R_5$ together are optionally substituted with one or two substituents independently selected from the group consisting of
$C_{1-8}$ alkyl;
$C_{1-8}$ alkoxy;
cyano;
nitro;
carboxy;
$C_{1-8}$ alkoxycarbonyl;
halo;
$C_{3-8}$ cycloalkyl;
aryl; and
heterocycle,
A is selected from the group consisting of
—O—;
—S(O)$_t$—, wherein t is zero to two, and
—NR$_6$—, and
X is —NR$_6$—,
or a pharmaceutically acceptable salt, ester or prodrug thereof.

8. A compound of claim 1 of formula (I)

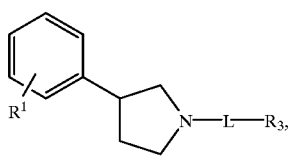

(I)

wherein
$R_1$ represents 1 or more optional substituents independently selected from the group consisting of
$C_{1-8}$ alkyl;
$C_{2-8}$ alkenyl;
$C_{2-8}$ alkynyl;
alkoxyalkyl, wherein the alkyl and alkylene groups are independently $C_{1-8}$;

$C_{1-8}$ alkoxy;
$C_{1-8}$ alkoxycarbonyl;
hydroxy;
$C_{1-8}$ hydroxyalkyl;
carboxy;
O-protected carboxy;
$C_{1-8}$ carboxyalkyl;
O-protected $C_{1-8}$ carboxyalkyl;
halo;
amino;
N-protected amino;
$C_{1-8}$ aminoalkyl; and
$C_{1-8}$ N-protected aminoalkyl;
L is $C_{2-8}$ alkylene; and
$R_3$ is

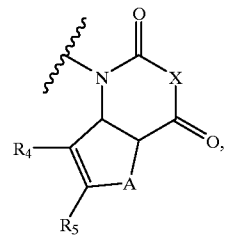

(5)

wherein $R_4$ and $R_5$ together form a ring which is fused to its adjacent ring and is selected from the group consisting of
(a) a five-membered carbocyclic ring and
(b) a five-membered ring having four carbon atoms and one heteroatom selected from the group consisting of
nitrogen,
oxygen, and
sulfur;
(c) a five-membered ring having three carbon atoms and two heteroatoms independently selected from the group consisting of
nitrogen,
oxygen, and
sulfur;
(d) a six-membered carbocyclic ring;
(e) a six-membered ring having five carbon atoms and one heteroatom selected from the group consisting of
nitrogen,
oxygen, and
sulfur;
(f) a six-membered ring having four carbon atoms and two heteroatoms selected from the group consisting of
nitrogen,
oxygen, and
sulfur;
(g) a six-membered ring having three carbon atoms and three heteroatoms selected from the group consisting of
nitrogen,
oxygen, and
sulfur;
wherein the five-membered rings formed b $R_4$ and $R_5$ together with the ring to which they are fused have 1 or 2 double bonds and wherein the six-membered rings formed by $R_4$ and $R_5$ together with the ring to which they are fused have 1, 2 or 3 double bonds, and wherein the rings formed b $R_4$ and $R_5$ together are optionally substituted with one or two substituents independently selected from the group consisting of $C_{1-8}$ alkyl;
$C_{1-8}$ alkoxy;
cyano,
nitro;
carboxy;
$C_{3-8}$ alkoxycarbonyl
halo;
$C_{3-8}$ cycloalkyl;
aryl; and
heterocycle, A is selected from the group consisting of
—O—;
—S(O)$_t$—, wherein t is zero to two and
—NR$_6$—, and X is —NR$_6$—,
or a pharmaceutically acceptable salt, ester or prodrug thereof.

9. A compound of claim 1 of formula (I)

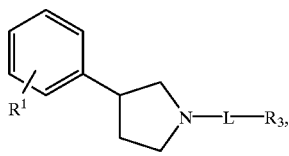

(I)

wherein
R$_1$ represents 1 or more optional substituents independently selected from the group consisting of
$C_{1-8}$ alkyl;
$C_{2-8}$ alkenyl;
$C_{2-8}$ alkynyl;
alkoxyalkyl, wherein the alkyl and alkylene groups are independently $C_{1-8}$g
$C_{1-8}$ alkoxy;
$C_{1-8}$ alkoxycarbonyl
hydroxy;
$C_{1-8}$ hydroxyalkyl;
carboxy;
O-protected carboxy,
$C_{1-8}$ carboxyalkyl;
O-protected $C_{1-8}$ carboxyalkyl;
halo;
amino;
N-protected amino;
$C_{1-8}$ aminoalkyl; and
$C_{1-8}$ N-protected aminoalkyl;

L is $C_{2-8}$ alkylene; and
R$_3$ is

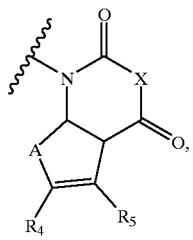

(6)

wherein R$_4$ and R$_5$ together form a ring which is fused to its adjacent ring and is selected from the group consisting of
(g) a five-membered carbocyclic ring and (b) a five-membered ring having four carbon atoms and one heteroatom selected from the group consisting of
nitrogen,
oxygen, and
sulfur;

(c) a five-membered ring having three carbon atoms and two heteroatoms independently selected from the group consisting of
nitrogen,
oxygen, and
sulfur;

(d) a six-membered carbocyclic ring;

(e) a six-membered ring having five carbon atoms and one heteroatom selected from the group consisting of
nitrogen,
oxygen, and
sulfur;

(f) a six-membered ring having four carbon atoms and two heteroatoms selected from the group consisting of
nitrogen,
oxygen, and
sulfur;

(g) a six-membered ring having three carbon atoms and three heteroatoms selected from the group consisting of
nitrogen,
oxygen, and
sulfur;

wherein the five-membered rings formed by R$_4$ and R$_5$ together with the ring to which they are fused have 1 or 2 double bonds, and wherein the six-membered rings formed by R$_4$ and R$_5$ together with the ring to which they are fused have 1, 2 or 3 double bonds and wherein the rings formed b R$_4$ and R$_5$ together are optionally substituted with one or two substituents independently selected from the group consisting of
$C_{1-8}$ alkyl;
$C_{1-8}$ alkoxy;
cyano;
carboxy;
$C_{1-8}$ alkoxycarbonyl
halo;
$C_{3-8}$ cycloalkyl;
aryl; and
heterocycle, A is selected from the group consisting of
—O—;
—S(O)$_t$—, wherein t is zero to two, and
—NR$_6$—, and X is —NR$_6$—,
or a pharmaceutically acceptable salt ester or prodrug thereof.

10. A pharmaceutical composition comprising a therapeutically effective amount of a compound of claim 1 in combination with a pharmaceutically acceptable carrier.

11. A method of antagonizing $\alpha_1$ adrenoreceptors in a host mammal in need of such treatment comprising administering a therapeutically effective amount of a compound of claim 1.

12. A method of treating benign prostatic hyperplasia (BPH) in a host mammal in need of such treatment comprising administering a therapeutically effective amount of a compound of claim 1.

13. A method of treating bladder outlet obstruction (BOO) in a host mammal in need of such treatment comprising administering a therapeutically effective amount of a compound of claim 1.

14. A method of treating neurogenic bladder in a host mammal in need of such treatment comprising administering a therapeutically effective amount of a compound of claim 1.

15. A method of treating uterine smooth muscle contraction in a host mammal in need of such treatment comprising administering a therapeutically effective amount of a compound of claim 1.

* * * * *